(12) United States Patent
Okazaki et al.

(10) Patent No.: US 7,022,689 B2
(45) Date of Patent: Apr. 4, 2006

(54) 5-AMIDINO-N-(2-AMINOPHENETHYL)-N-HYDROXY-BENZENESULFFONAMIDE DERIVATIVE, MEDICAL COMPOSITION CONTAINING THE SAME, PHARMACEUTICAL USE THEREOF AND INTERMEDIATE THEREFOR

(75) Inventors: Kosuke Okazaki, Nagano (JP); Masahiko Uchida, Nagano (JP); Hiroaki Kobayashi, Nagano (JP); Yuichiro Kai, Nagano (JP); Hideki Takeuchi, Nagano (JP); Kenji Yokoyama, Nagano (JP); Yoshihiro Terao, Nagano (JP); Ritsu Suzuki, Nagano (JP)

(73) Assignee: Kissei Pharmaceutical Co., Ltd., Nagano (JP)

( * ) Notice: Subject to any disclaimer, the term of this patent is extended or adjusted under 35 U.S.C. 154(b) by 0 days.

(21) Appl. No.: 10/486,137

(22) PCT Filed: Aug. 8, 2002

(86) PCT No.: PCT/JP02/08093

§ 371 (c)(1),
(2), (4) Date: Feb. 6, 2004

(87) PCT Pub. No.: WO03/016269

PCT Pub. Date: Feb. 27, 2003

(65) Prior Publication Data

US 2004/0242455 A1    Dec. 2, 2004

(30) Foreign Application Priority Data

Aug. 9, 2001 (JP) .............................. 2001-242905

(51) Int. Cl.
*A01N 43/00* (2006.01)
*A61K 31/33* (2006.01)
(52) U.S. Cl. .......................................... 514/183; 514/1
(58) Field of Classification Search ................ 514/183, 514/1
See application file for complete search history.

(56) References Cited

FOREIGN PATENT DOCUMENTS

| WO | WO 97/30971 | 8/1997 |
| WO | WO 00/59876 | * 10/2000 |
| WO | WO 02/28827 A1 | 4/2002 |

* cited by examiner

*Primary Examiner*—Johann Richter
*Assistant Examiner*—Chukwuma Nwaonicha
(74) *Attorney, Agent, or Firm*—Sughrue Mion, PLLC

(57) ABSTRACT

The present invention relates to a 5-amidino-N-(2-aminophenethyl)-2-hydroxybenzenesulfonamide derivative represented by the general formula:

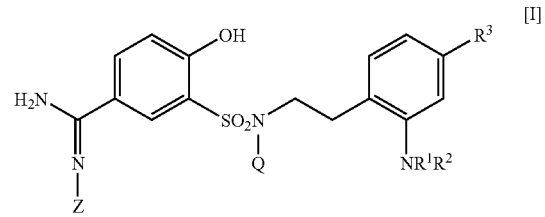

wherein $R^1$ is a hydrogen atom or a lower alkyl group;
$R^2$ represents a hydrogen atom, an optionally substituted lower alkyl group, etc.;
$R^3$ is a di(lower alkyl)amino group, a lower alkyl group, a cycloalkyl group, etc.;
Q is a hydrogen atom or an optionally substituted lower alkyl group; and
Z is a hydrogen atom or a hydroxy group, etc.,
or a pharmaceutically acceptable salt thereof, which exerts a potent and selective activated blood coagulation factor X inhibitory activity and is useful as an agent for the prevention or treatment of a disease occurred associating an activated blood coagulation factor X, a pharmaceutical composition comprising the same, a pharmaceutical use thereof and an intermediate thereof.

24 Claims, No Drawings

5-AMIDINO-N-(2-AMINOPHENETHYL)-N-HYDROXY-BENZENESULFFONAMIDE DERIVATIVE, MEDICAL COMPOSITION CONTAINING THE SAME, PHARMACEUTICAL USE THEREOF AND INTERMEDIATE THEREFOR

TECHNICAL FIELD

The present invention relates to novel 5-amidino-N-(2-aminophenethyl)-2-hydroxybenzenesulfonamide derivatives or pharmaceutically acceptable salts thereof which are useful as medicaments.

More particularly, the present invention relates to 5-amidino-N-(2-aminophenethyl)-2-hydroxybenzenesulfonamide derivatives or pharmaceutically acceptable salts thereof, which exert an excellent inhibitory activity on activated blood coagulation factor X and are useful as activated blood coagulation factor X inhibitors, pharmaceutical compositions comprising the same, their pharmaceutical uses and intermediates for their preparation.

BACKGROUND ART

The anticoagulation therapy has been extensively performed for the prevention and treatment of thromboembolic diseases caused by blood hypercoagulability, and drugs such as heparin and warfarin potassium have been frequently used as anticoagulant agents at present.

However, heparin shows inhibitory activity on thrombin and activated blood coagulation factor X, and has been known to have a risk of causing bleeding tendency.

Warfarin potassium is an anticoagulant which controls biosynthesis of vitamin K-dependent coagulation factor, and it is difficult to control the anticoagulation capacity due to its action mechanism when this drug is used in the prevention and treatment of thromboembolic diseases. Therefore, this drug is extremely hard to use clinically.

In recent years, selective thrombin inhibitors have been developed and have been used clinically. However, since thrombin plays a close part in the conversion of fibrinogen into fibrin in blood coagulation cascade reactions and platelet activation and aggregation, the thrombin inhibitors have similar disadvantages to heparin on the point of view of the safety such as bleeding tendency. Moreover, it has been reported that their efficacies are not necessarily sufficient.

On the other hand, activated blood coagulation factor X, which acts at the juncture of the extrinsic and intrinsic blood coagulation cascade reactions, located on the upstream of thrombin, so that an anticoagulation activity of activated blood coagulation factor X is more efficient than that of thrombin inhibitors. Therefore, activated blood coagulation factor X inhibitors attract public attentions as drugs having a possibility to inhibit the coagulation system effectively.

Furthermore, with the changing into European and American life styles and the aging of population have been developed in recent years, incidences of thromboembolic diseases such as myocardial infarction and arteriovenous obstruction will go on increasing, and therefore, the social importance of more efficient anticoagulants has been going on increasing, and the demands on development of such anticoagulants are great.

DISCLOSURE OF THE INVENTION

The present inventors have studied hard to find novel compounds having an excellent inhibitory activity on activated blood coagulation factor X. As a result, it was surprisingly found that certain 5-amidino-N-(2-aminophenethyl)-2-hydroxybenzenesulfonamide derivatives show a potent and selective activated blood coagulation factor X inhibitory activity, thereby forming the basis of the present invention.

The present invention is to provide novel compounds which exert a potent and selective activated blood coagulation factor X inhibitory activity.

This is, the present invention relates to a 5-amidino-N-(2-aminophenethyl)-2-hydroxybenzenesulfonamidemide derivative represented by the general formula:

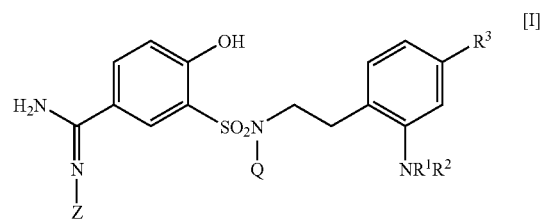

wherein $R^1$ represents a hydrogen atom or a lower alkyl group;

$R^2$ represents a hydrogen atom, a lower alkyl group, $-Y^1-COOR^A$ in which $Y^1$ represents a lower alkylene group or a single bond;

and $R^A$ represents a hydrogen atom or a lower alkyl group, $-COCOOR^B$ in which $R^B$ represents a hydrogen atom or a lower alkyl group, $-Y^2-CONH-R^C$ in which $Y^2$ represents a lower alkylene group or a single bond; and $R^C$ represents a hydrogen atom, or a lower alkyl group which may have a substituent selected from the following group (i), $-COCONH-R^D$ in which $R^D$ is a hydrogen atom or a lower alkyl group which may have a substituent selected from the following group (ii), $-CO-Y^3-R^E$ in which $Y^3$ is a lower alkylene group or a single bond; and $R^E$ represents a 5 to 10-membered aromatic heterocyclic group which may have a lower alkyl group, $-CO-Y^4-R^F$ in which $Y^4$ is a lower alkylene group which may have one or two hydroxy groups; and $R^F$ represents a $-CO-OR^{F1}$ in which $R^{F1}$ is a hydrogen atom or a lower alkyl group, or a lower alkylsulfonyl group which may have $-COOR^G$ where $R^G$ is a hydrogen atom or a lower alkyl group;

(i) $-COOR^{C1}$ in which $R^{C1}$ is a hydrogen atom or a lower alkyl group;

(ii) $-COOR^{D1}$ in which $R^{D1}$ is a hydrogen atom or a lower alkyl group;

$R^3$ represents a di (lower alkyl) amino group, a lower alkyl group, a 3 to 10-membered cycloalkyl group, a 6 to 10-membered aryl group which may have one to three substituents selected from the following group (A), a 3 to 10-membered heterocycloalkyl group which may have an oxo group, or a 5 to 10-membered aromatic heterocyclic group which may have a substituent selected from the following group (B);

(A) an oxo group, a lower alkyl group, a halo(lower alkyl) group, $-Y^5-R^H$, a halogen atom, a nitro group, an amino group, $-COOR^I$, a carbamoyl group, a sulfamoyl group, a lower alkylsulfonyl group, a mono(lower alkyl)sulfamoyl group which may have $-COOR^J$, and a lower alkylsulfonylamino-substituted (lower alkyl) group;

wherein Y⁵ represents an oxygen atom or a sulfur atom;
R^H represents a hydrogen atom, a halo(lower alkyl) group or a lower alkyl group which may have —COOR^{H1} in which R^{H1} is a hydrogen atom, a 3 to 10-membered heterocycloalkyl group or a lower alkyl group;
R^I represents a hydrogen atom, a 3 to 10-membered cycloalkyl group or a lower alkyl group;
R^J represents a hydrogen atom, a 3 to 10-membered cycloalkyl group or a lower alkyl group;
(B) a lower alkyl group, an amino group and —COOR^K wherein R^K represents a hydrogen atom, a 3 to 10-membered cycloalkyl group and lower alkyl group;

Q represents a hydrogen atom or a lower alkyl group which may have a substituent selected from the following group (C);
(C) —OR^L, —COOR^M, —CONR^N R^O, a 6 to 10-membered aryl group which may have one to three substituents selected from the following group (iii), and a 5 to 10-membered aromatic heterocyclic group which may have one to three substituents selected from the following group (iv);
wherein R^L represents a hydrogen atom or a lower alkyl group which may have —OR^{L1} where R^{L1} represents a hydrogen atom or a lower alkyl group;
R^M represents a hydrogen atom, a 3 to 10-membered cycloalkyl group, or a lower alkyl group which may have a substituent selected from the following group (v);
R^N and R^O independently represent a hydrogen atom, a 6 to 10-membered aryl group which may have a carbamoyl group, a 5 to 10-membered aromatic heterocyclic group which may have a substituent selected from the following group (vi), or a lower alkyl group which may have a substituent selected from the following group (vii), or —NR^N R^O forms a cyclic amino group which may have a substituent selected from the following group (viii);
(v) —COOR^{M1} in which R^{M1} is a hydrogen atom, a 3 to 10-membered cycloalkyl group or a lower alkyl group, —OCOR^{M2} in which R^{M2} is a 3 to 10-membered cycloalkyl group or a lower alkyl group, —OCOOR^{M3} in which R^{M3} is a 3 to 10-membered cycloalkyl group or a lower alkyl group, —OR^{M4} in which R^{M4} is a hydrogen atom, a 3 to 10-membered cycloalkyl group or a lower alkyl group, —CONR^{M5}R^{M6} in which R^{M5} and R^{M6} are independently a hydrogen atom or a lower alkyl group, or —NR^{M5}R^{M6} forms a cyclic amino group, a 3 to 10-membered cycloalkyl group, a 6 to 10-membered aryl group, a 3 to 10-membered heterocycloalkyl group, and a 5 to 10-membered aromatic heterocyclic group;
(vi) a halogen atom, a lower alkyl group, a carbamoyl group and —COOR^{N1} in which R^{N1} represents a hydrogen atom, or a lower alkyl group;
(vii) —OR^{N2} in which R^{N2} is a hydrogen atom or a lower alkyl group, and a 5 to 10-membered aromatic heterocyclic group;
(viii) a hydroxy group, a lower alkyl group, a hydroxy(lower alkyl) group, a carbamoyl group, a di(lower alkyl)amino group, a lower acyl group, and —COOR^{N3} in which R^{N3} represents a hydrogen atom or a lower alkyl group;
(iii) a halogen atom, a nitro group, a lower alkyl group, —OR^P in which R^P is a hydrogen atom or a lower alkyl group, and —COOR^Q in which R^Q is a hydrogen atom or a lower alkyl group;
(iv) a halogen atom, an oxo group, a lower alkyl group and a phenyl group; and Z represents a hydrogen atom, a hydroxy group or —COOR^R; wherein R^R is a halo(lower alkyl) group, a 6 to 10-membered aryl group or a lower alkyl group which may have a substituent selected from the following group (ix);
(ix) —OR^{R1} in which R^{R1} is a hydrogen atom or a lower alkyl group, —COOR^{R2} in which R^{R2} is a lower alkyl group which may have —COOR^{R2} where R^{R2} is a lower alkyl group, —CONR^{R3}R^{R4} in which R^{R3} and R^{R4} are independently a hydrogen atom or a lower alkyl group, or —NR^{R3}R^{R4} forms a cyclic amino group, —OCOR^{R5} in which R^{R5} is a lower alkyl group which may have —OCOR^{R51} where R^{R51} is a lower alkyl group, a 3 to 10-membered heterocycloalkyl group and a 6 to 10-membered aryl group;

or a pharmaceutically acceptable salt thereof.

The present invention also relates to a pharmaceutical composition comprising as an active ingredient a 5-amidino-N-(2-aminophenethyl)-2-hydroxybenzenesulfonamide derivative represented by the above general formula (I) or a salt thereof.

The present invention relates to an activated blood coagulation factor X inhibitor comprising as an active ingredient a 5-amidino-N-(2-aminophenethyl)-2-hydroxybenzenesulfonamide derivative represented by the above general formula (I) or a pharmaceutically acceptable salt thereof.

The present invention relates to an agent for the prevention or treatment of a disease occurred associating an activated blood coagulation factor X, which comprises as an active ingredient a 5-amidino-N-(2-aminophenethyl)-2-hydroxybenzenesulfonamide derivative represented by the above general formula (I) or a pharmaceutically acceptable salt thereof.

The present invention relates to a method for the prevention or treatment of a disease occurred associating an activated blood coagulation factor X, which comprises administering a therapeutically effective amount of a 5-amidino-N-(2-aminophenethyl)-2-hydroxybenzenesulfonamide derivative represented by the above general formula (I) or a pharmaceutically acceptable salt thereof.

The present invention relates to a use of a 5-amidino-N-(2-aminophenethyl)-2-hydroxybenzenesulfonamide derivative represented by the above general formula (I) or a pharmaceutically acceptable salt thereof for the manufacture of a pharmaceutical composition for the prevention or treatment of a disease occurred associating an activated blood coagulation factor X.

The present invention relates to a pharmaceutical composition which comprises (a) a 5-amidino-N-(2-aminophenethyl)-2-hydroxybenzenesulfonamide derivative represented by the above general formula (I) or a pharmaceutically acceptable salt thereof, and (b) at least one member selected from the group consisting of adrenocortical hormone, antiplatelet drugs, adenylate cyclase activators, PGF2α antagonists, cyclooxygenase inhibitors, adenosine antagonists, GPIIb/IIIa antagonists, anticoagulants, thrombolitic drugs, antithrombin drugs, free-radical scavengers, immunosuppressants, erythropoietin, fish oil, angiotensin-converting enzyme inhibitors, angiotensin II receptor antagonists, glycation inhibitors, protein C kinase inhibitors, aldose reductase inhibitors, endothelin receptor antagonists, endothelin-converting enzyme inhibitors, neutral endopeptidase inhibitors, thromoxane A₂ synthetase inhibitors, thromboxane A₂ receptor antagonists and PGI₂ agonists.

The present invention relates to an agent for the prevention or treatment of a disease occurred associating an activated blood coagulation factor X, which comprises as an active ingredient (a) a 5-amidino-N-(2-aminophenethyl)-2-hydroxybenzenesulfonamide derivative represented by the above general formula (I), a pharmaceutically acceptable salt thereof, and (b) at least one member selected from the group consisting of adrenocortical hormone, platelet aggregation inhibitors, adenylate cyclase activators, PGF2α antagonists, cyclooxygenase inhibitors, adenosine antagonists, GPIIb/IIIa antagonists, anticoagulants, thrombolitic drugs, antithrombin drugs, free-radical scavengers, immunosuppressants, erythropoietin, fish oil, angiotensin-converting enzyme inhibitors, angiotensin II receptor antagonists, glycation inhibitors, protein C kinase inhibitors, aldose reductase inhibitors, endothelin receptor antagonists, endothelin-converting enzyme inhibitors, neutral endopeptidase inhibitors, thromoxane A₂ synthetase inhibitors, thromboxane A₂ receptor antagonists and PGI₂ agonists.

The present invention relates to a method for the prevention or treatment of a disease occurred associating an activated blood coagulation factor X, which comprises administering a therapeutically effective amount of (a) a 5-amidino-N-(2-aminophenethyl)-2-hydroxybenzenesulfonamide derivative represented by the above general formula (I) or a pharmaceutically acceptable salt thereof, and (b) at least one member selected from the group consisting of adrenocortical hormone, platelet aggregation inhibitors, adenylate cyclase activators, PGF2α antagonists, cyclooxygenase inhibitors, adenosine antagonists, GPIIb/IIIa antagonists, anticoagulants, thrombolitic drugs, antithrombin drugs, free-radical scavengers, immunosuppressants, erythropoietin, fish oil, angiotensin-converting enzyme inhibitors, angiotensin II receptor antagonists, glycation inhibitors, protein C kinase inhibitors, aldose reductase inhibitors, endothelin receptor antagonists, endothelin-converting enzyme inhibitors, neutral endopeptidase inhibitors, thromoxane A₂ synthetase inhibitors, thromboxane A₂ receptor antagonists and PGI₂ agonists.

The present invention relates to a use of (a) a 5-amidino-N-(2-aminophenethyl)-2-hydroxybenzenesulfonamide derivative represented by the above general formula (I) or a pharmaceutically acceptable salt thereof, and (b) at least one member selected from the group consisting of adrenocortical hormone, platelet aggregation inhibitors, adenylate cyclase activators, PGF2α antagonists, cyclooxygenase inhibitors, adenosine antagonists, GPIIb/IIIa antagonists, anticoagulants, thrombolitic drugs, antithrombin drugs, free-radical scavengers, immunosuppressants, erythropoietin, fish oil, angiotensin-converting enzyme inhibitors, angiotensin II receptor antagonists, glycation inhibitors, protein C kinase inhibitors, aldose reductase inhibitors, endothelin receptor antagonists, endothelin-converting enzyme inhibitors, neutral endopeptidase inhibitors, thromoxane A₂ synthetase inhibitors, thromboxane A₂ receptor antagonists and PGI₂ agonists, for the manufacture of a pharmaceutical composition for the prevention or treatment of a disease occurred associating an activated blood coagulation factor X.

Furthermore, the present invention relates to a 5-cyano-N-(2-aminophenethyl)-2-hydroxybenzenesulfonamide derivative represented by the general formula:

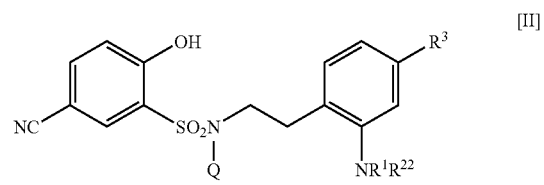

wherein $R^1$ represents a hydrogen atom or a lower alkyl group;
$R^{22}$ represents a hydrogen atom, a lower alkyl group, —$Y^1$—COOR$^A$ in which $Y^1$ represents a lower alkylene group or a single bond; and $R^A$ represents a hydrogen atom, or a lower alkyl group, —COCOOR$^B$ in which $R^B$ represents a hydrogen atom or lower alkyl group, —$Y^2$—CONH—R$^C$ in which $Y^2$ represents a lower alkylene group or a single bond; and $R^C$ represents a hydrogen atom, or a lower alkyl group which may have a substituent selected from the following group (i), —COCONH—R$^D$ in which $R^D$ is a hydrogen atom or a lower alkyl group which may have a substituent selected from the following group (ii), —CO—$Y^3$—R$^E$ in which $Y^3$ is a lower alkylene group or a single bond; and $R^E$ represents a 5 to 10-membered aromatic heterocyclic group which may have a lower alkyl group, —CO—$Y^{41}$—R$^F$ in which $Y^{41}$ is a lower alkylene group which may have one or two optionally protected hydroxy groups; and $R^F$ represents —COOR$^{F1}$ in which $R^{F1}$ is a hydrogen atom or a lower alkyl group or a lower alkyl group which may have —COOR$^G$ in which $R^G$ is a hydrogen atom or a lower alkylsulfonyl group;
(i) —COOR$^{C1}$ in which $R^{C1}$ is a hydrogen atom and a lower alkyl group;
(ii) —COOR$^{D1}$ in which $R^{D1}$ is a hydrogen atom and a lower alkyl group;
$R^3$ represents a di(lower alkyl) amino group, a lower alkyl group, a 3 to 10-membered cycloalkyl group, a 6 to 10-membered aryl group which may have one to three substituents selected from the following group (A), a 3 to 10-membered heterocycloalkyl group which may have an oxo group or a 5 to 10-membered aromatic heterocyclic group which may have a substituent selected from the following group (B);
(A) an oxo group, a lower alkyl group, a halo (lower alkyl) group, —$Y^5$—R$^H$, a halogen atom, a nitro group, an amino group, —COOR$^I$, a carbamoyl group, a sulfamoyl group, a lower alkylsulfonyl group, a mono (lower alkyl)sulfamoyl group which may have —COOR$^J$, and a lower alkylsulfonylamino-substituted (lower alkyl) group;
wherein $Y^5$ represents an oxygen atom or a sulfur atom;
$R^H$ represents a hydrogen atom, a halo(lower alkyl) group, or a lower alkyl group which may have —COOR in which $R^{H1}$ is a hydrogen atom, a 3 to 10-membered cycloalkyl group or a lower alkyl group;
$R^I$ represents a hydrogen atom or a 3 to 10-membered cycloalkyl group or a lower alkyl group;
$R^J$ represents a hydrogen atom, a 3 to 10-membered cycloalkyl group or a lower alkyl group;
(B) a lower alkyl group, an amino group and —COOR$^K$;
wherein $R^K$ represents a hydrogen atom, a 3 to 10-membered cycloalkyl group or a lower alkyl group;

Q represents a hydrogen atom or a lower alkyl group which may have a substituent selected from the following group (C);

(C) —$OR^L$, —$COOR^M$, —$CONR^N R^O$ a 6 to 10-membered aryl group which may have one to three substituents selected from the following group (iii), and a 5 to 10-membered aromatic heterocyclic group which may have one to three substituents selected from the following group (iv); wherein $R^L$ represents a hydrogen atom or a lower alkyl group which may have —$OR^{L1}$ where $R^{L1}$ represents a hydrogen atom or a lower alkyl group;

$R^M$ represents a hydrogen atom, a 3 to 10-membered cycloalkyl group, or a lower alkyl group which may have a substituent selected from the following group (v);

$R^N$ and $R^O$ independently represent a hydrogen atom, a 6 to 10-membered aryl group which may have a carbamoyl group, a 5 to 10-membered aromatic heterocyclic group which may have a substituent selected from the following group (vi), or a lower alkyl group which may have a substituent selected from the following group (vii), or —$NR^N R^O$ forms a cyclic amino group which may have a substituent selected from the following group (viii);

(v) —$COOR^{M1}$ in which $R^{M1}$ is a hydrogen atom, a 3 to 10-membered cycloalkyl group or a lower alkyl group, —$OCOR^{M2}$ in which $R^{M2}$ is a 3 to 10-membered cycloalkyl group or a lower alkyl group, —$OCOOR^{M3}$ in which $R^{M3}$ is a 3 to 10-membered cycloalkyl group or a lower alkyl group, —$OR^{M4}$ in which $R^{M4}$ is a hydrogen atom, a 3 to 10-membered cycloalkyl group or a lower alkyl group, —$CONR^{M5}R^{M6}$ in which $R^{M5}$ and $R^{M6}$ are independently a hydrogen atom or a lower alkyl group, or —$NR^{M5}R^{M6}$ forms a cyclic amino group, a 3 to 10-membered cycloalkyl group, a 6 to 10-membered aryl group, a 3 to 10-membered heterocycloalkyl group, and a 5 to 10-membered aromatic heterocyclic group;

(vi) a halogen atom, a lower alkyl group, a carbamoyl group and —$COOR^{N1}$ in which $R^{N1}$ represents a hydrogen atom, or a lower alkyl group;

(vii) —$OR^{N2}$ in which $R^{N2}$ is a hydrogen atom or a lower alkyl group, and a 5 to 10-membered aromatic heterocyclic group;

(viii) a hydroxy group, a lower alkyl group, a hydroxy(lower alkyl) group, a carbamoyl group, a di(lower alkyl)amino group, a lower acyl group, and —$COOR^{N3}$ in which $R^{N3}$ represents a hydrogen atom or a lower alkyl group;

(iii) a halogen atom, a nitro group, a lower alkyl group, —$OR^P$ in which $R^P$ is a hydrogen atom or a lower alkyl group, and —$COOR^Q$ in which $R^Q$ is a hydrogen atom or a lower alkyl group;

(iv) a halogen atom, an oxo group, a lower alkyl group and a phenyl group;

or a pharmaceutically acceptable salt thereof.

In the present invention, the term "lower alkyl group" means a straight-chained or branched alkyl group having 1 to 6 carbon atoms such as a methyl group, an ethyl group, a propyl group, an isopropyl group, a butyl group, an isobutyl group, a sec-butyl group, a pentyl group, an isopentyl group, a neopentyl group, a 1-methylbutyl group, a 2-methylbutyl group, a hexyl group or the like. The term "lower alkylsulfonyl group" means a sulfonyl group having the above lower alkyl group, such as a methanesulfonyl group, an ethanesulfonyl group, a propanesulfonyl group, an isopropanesulfonyl group, a butanesulfonyl group, an isobutanesulfonyl group, a sec-butanesulfonyl group, a pentanesulfonyl group, an isopentanesulfonyl group, a neopentanesulfonyl group, a hexanesulfonyl group or the like. The term "mono(lower alkyl)sulfamoyl group" means a monoalkylsulfamoyl group wherein the alkyl moiety is the same as the above lower alkyl group. The term "di(lower alkyl)amino group" means an amino group di-substituted by same or different lower alkyl groups as defined above. The term "lower alkylsulfonylamino-substituted (lower alkyl) group" means the above alkyl group having an amino group N-substituted by the above lower alkylsulfonyl group. The term "hydroxy(lower alkyl) group" means a straight-chained or branched alkyl group having 2 to 6 carbon atoms and substituted by a hydroxy group. The term "lower acyl group" means a straight-chained or branched alkylcarbonyl group having 2 to 6 carbon atoms such as an acetyl group, a propionyl group, a butyryl group, an isobutyryl group, a valeryl group, a hexanoyl group or the like. The term "lower alkylene group" means a straight-chained or branched alkylene group having 1 to 6 carbon atoms such as a methylene group, an ethylene group, a trimethylene group, a propylene group or the like.

The term "3 to 10-membered cycloalkyl group" means a 3 to 7-membered monocyclic aliphatic alkyl group such as a cyclopropyl group, a cyclobutyl group, a cyclopentyl group, a cyclohexyl group or a cycloheptyl group, or a cyclopentyl group or a cyclohexyl group which are fused with a benzene ring. The term "6 to 10-membered aryl group" means a phenyl group, a naphthyl group, or a phenyl group which is fused with a cyclopentane ring or a cyclohexane ring.

The term "3 to 10-membered heterocycloalkyl group" means a 3 to 7-membered monocyclic heteroalkyl group containing one to two hetero atoms selected from a nitrogen atom, an oxygen atom and a sulfur atom in the ring, or a bicyclic heteroalkyl group which is benzene-fused 5 or 6-membered monocyclic heteroalkyl group as defined above, and as examples of such groups, for example, a monovalent group derived from morpholine, thiomorpholine, pyrrolidine, imidazoline, oxazoline, piperidine, piperazine, tetrahydrofuran, aziridine, azetidine, indoline, isoindoline, chroman, isochroman or the like can be illustrated. As examples of heterocycloalkyl group having an oxo group, for example, a monovalent group derived from a 2-oxazolidone or the like.

The term "5 to 10-membered aromatic heterocyclic group" means a 5 to 6-membered monocyclic aromatic group containing one to four hetero atoms selected from a nitrogen atom, an oxygen atom and a sulfur atom in the ring, or a bicyclic heteroalkyl group which is benzene or pyridine-fused 5 or 6-membered monocyclic aromatic group as defined above, and as examples of such groups, for example, a monovalent group derived from pyridine, pyrimidine, pyrazine, pyridazine, pyrrole, thiophene, oxazole, thiazole, imidazole, pyrazole, oxadiazole, thiodiazole, tetrazole, indole, indolizine, benzofuran, benzothiophene, quinoline, isoquinoline, phthalazine, naphthyridine, quinoxaline, quinazoline, cinnoline or the like can be illustrated. As examples of aromatic heterocyclic group having an oxo group, for example, a monovalent group derived from a 1,3,4-oxadiazol-2-one or the like can be illustrated.

The term "cyclic amino group" means a 5 to 6-membered monocyclic amino group which may contain one hetero atom selected from a nitrogen atom, an oxygen atom and a sulfur atom other than the nitrogen atom at the binding site in the ring, such as a 1-pyrrolodinyl group, a piperidino group, a morpholino group, a thiomorpholino group, a 1-piperazinyl group or the like.

The term "halogen atom" means a fluorine atom, a chlorine atom, a bromine atom or an iodine atom. The term "halo(lower alkyl) group" means the above alkyl group substituted by one to three halogen atom as defined above, such as a trifluoromethyl group, a 2,2,2-trifluoroethyl group or the like.

The term "hydroxy-protective group" means a hydroxy-protective group used generally in organic synthesis, which is described in PROTECTIVE GROUPS IN ORGANIC SYNTHESIS, THEODORA W. GREENE, PETER G. WUTS by JOHN WILEY&SONS, INC, such as a benzyl group, a methoxymethyl group, an acetyl group or the like.

For example, the compounds represented by the above general formula (I) of the present invention can be prepared by allowing a 5-cyano-N-(2-aminophenethyl)-2-hydroxy-benzenesulfonamide derivative represented by the above general formula (II) or a salt thereof to react with an alcohol in the presence of hydrogen chloride (hereinafter referred to as Process 1), allowing the resulting compound to react with ammonia or a salt thereof, or hydroxylamine or a salt thereof (hereinafter referred to as Process 2), carrying out, as occasion demands, suitably one to four processes selected from the group consisting of (1) hydrolysis of the resulting ester group (hereinafter referred to as Process 3), (2) ester interchange or esterification of the resulting compound using an alcohol compound represented by the general formula:

$$R^S\text{—OH} \quad [\text{III}]$$

wherein $R^S$ represents a 3 to 10-membered cycloalkyl group or a lower alkyl group which may have a substituent selected from the above group (v), or esterification of the resulting compound using a compound represented by the general formula:

$$R^S\text{—}X^1 \quad [\text{IV}]$$

wherein X represents a leaving group such as a halogen atom, a toluenesulfonyloxy group, a methanesulfonyloxy group or the like; and $R^S$ has the same meaning as defined above (hereinafter referred to as Process 4), (3) introduction of a protective group into a phenolic hydroxy group (hereinafter referred to as Process 5) and (4) N-acylation of the resulting compound using a compound represented by the general formula:

$$R^R\text{OCO}\text{—}X^2 \quad [\text{V}]$$

wherein X represents a leaving group such as a halogen atom, a 4-nitrophenoxy group or the like; and $R^R$ has the same meaning as defined above, and subjecting, as occasion demands, to removal of the protective group of the phenolic hydroxy group or O-deacylation in the usual way.

In the aforementioned production process, the reaction from a 5-cyano-N-(2-aminophenethyl)-2-hydroxybenzene-sulfonamide derivative represented by the above general formula (II) into a 5-amidino-N-(2-aminophenethyl)-2-hydroxybenzenesulfonamide derivative represented by the above general formula (I) is as follows in detail.

Process 1

A corresponding imidate compound can be prepared by allowing a 5-cyano-2-hydroxybenzenesulfonamide derivative represented by the above general formula (II) to react with an alcohol such as methanol or ethanol in the presence of a hydrogen halide such as hydrogen chloride or hydrogen bromide at usually −20° C. to room temperature. As a solvent used, methanol, ethanol, a mixed solvent of such alcohol with tetrahydrofuran, dichloromethane or N,N-dimethylformamide, and the like can be illustrated. The reaction time is usually from 1 hour to 3 days, varying based on sorts and volumes of a used starting material and solvent.

Process 2

A corresponding amidino compound can be prepared by allowing an imidate compound to react with ammonia or an ammonium salt such as ammonium carbonate, ammonium chloride or ammonium acetate, or hydroxylamine or a salt thereof in the presence or absence of a base such as triethylamine at usually 0° C. to room temperature. As a solvent used, methanol, ethanol, tetrahydrofuran, dichloromethane and the like can be illustrated. The reaction time is usually from 1 hour to 3 days, varying based on sorts and volumes of a used starting material and solvent.

Process 3

In case of compounds having an ester group in the amidino derivatives obtained by Process 2, a corresponding carboxylic acid compound can be prepared by subjecting such compound to hydrolysis using an acid such as hydrochloric acid or sulfuric acid at usually room temperature to reflux temperature, or a base such as sodium hydroxide at usually 0° C. to reflux temperature. As a solvent used, water, acetonitrile, tetrahydrofuran, alcohols, a mixed solvent thereof and the like can be illustrated. The reaction time is usually from 1 hour to 2 days, varying based on sorts and volumes of a used starting material and solvent.

Process 4

A corresponding ester compound can be prepared by 1) subjecting an amidino derivative having an ester group or a carboxy group obtained by Process 2 or 3 to ester interchange or esterification using an alcohol compound represented by the above general formula (III) in the presence of an acid such as hydrochloric acid, sulfuric acid or p-toluenesulfonic acid at usually 0° C. to reflux temperature, by 2) subjecting a compound having a carboxy group of the amidino derivatives obtained by Process 2 or 3 to esterification using an alcohol compound represented by the above general formula (III) in the presence of a condensing agent such as 1-(3-dimethylaminopropyl)-3-ethylcarbodiimide hydrochloride at usually 0° C. to reflux temperature, or by 3) subjecting a compound having a carboxy group of the amidino derivatives obtained by Process 2 or 3 to esterification using a compound represented by the above general formula (IV) in the presence of a base such as potassium carbonate or triethylamine, or silver carbonate at usually 0° C. to reflux temperature. As a solvent used, an aprotic solvent such as tetrahydrofuran and the like can be illustrated. The reaction time is usually from 1 hour to 2 days, varying based on sorts and volumes of a used starting material and solvent.

Process 5

A corresponding O-protected compound can be prepared by suitably protecting a phenolic hydroxy group of a compound having an amidino group obtained by Processes 2 to 4 according to a method described in PROTECTIVE GROUPS IN ORGANIC SYNTHESIS, THEODORA W. GREENE, PETER G. WUTS by JOHN WILEY&SONS, INC.

Process 6

A corresponding carbamate compound can be prepared by allowing a compound having an amidino group obtained by Processes 2–5 to react with a compound represented by the above general formula (V) in the presence of a base such as triethylamine or diisopropylethylamine at usually 0° C. to room temperature. As a solvent used, N,N-dimethylformamide and the like can be illustrated. The reaction time is usually from 1 hour to 2 days, varying based on sorts and volumes of a used starting material and solvent.

The removal of the protective group of the hydroxy group can be commonly carried out according to a method described in PROTECTIVE GROUPS IN ORGANIC SYNTHESIS, THEODORA W. GREENE, PETER G. WUTS by JOHN WILEY&SONS, INC.

Of the compounds represented by the above general formula (I), a compound represented by the general formula:

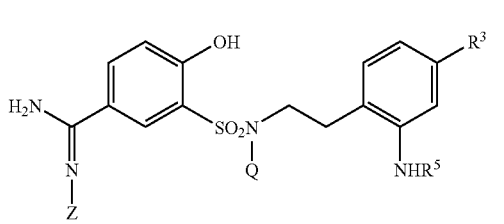

[Ia]

wherein $R^5$ represents —$Y^2$—CONH—$R^C$ in which $Y^2$ and $R^C$ have the same meanings as defined above or —CO-CONH—$R^D$ in which $R^D$ has the same meanings as defined above; and $R^3$, Q, and Z have the same meanings as defined above, can be prepared by allowing a compound represented by the general formula:

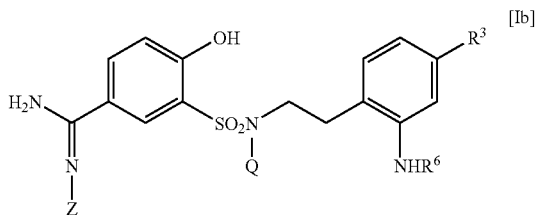

[Ib]

wherein $R^6$ represents —$Y^2$—COOH in which $Y^2$ has the same meanings as defined above or —COOH; and $R^3$, Q and Z have the same meanings as defined above, or a salt thereof to react in the presence of a condensing agent with an amine compound represented by the general formula:

$$H_2NR^C$$ [VI]

wherein $R^C$ has the same meanings as defined above, or a salt thereof, or an amine compound represented by the general formula:

$$H_2NR^D$$ [VII]

wherein $R^D$ has the same meanings as defined above, or a salt thereof (hereinafter referred to as Process 7).

In the aforementioned production process, the reaction from a 5-amidino-N-(2-aminophenethyl)-2-hydroxybenzenesulfonamide derivative represented by the above general formula (Ib) into a 5-amidino-N-(2-aminophenethyl)-2-hydroxybenzenesulfonamide derivative represented by the above general formula (Ia) is as follows in detail.

Process 7

A 5-amidino-N-(2-aminophenethyl)-2-hydroxybenzenesulfonamide derivative represented by the above general formula (Ia) can be prepared by allowing a 5-amidino-N-(2-aminophenethyl)-2-hydroxybenzenesulfonamide derivative represented by the above general formula (Ib) or a salt thereof to react with an amine compound represented by the above general formula (VI) or a salt thereof, or an amine compound represented by the above general formula (VII) or a salt thereof in the presence of a condensing agent such as 1-(3-dimethylaminoproyl)-3-ethyl-carbodiimide hydrochloride, diphenylphoshoryl azide or the like and in the presence or absence of an agent for making an activated ester such as 1-hydroxybenzotriazole monohydrate and a base such as triethylamine at usually 0° C. to room temperature. As a solvent used, dichloromethane, N,N-dimethylformamide and the like can be illustrated. The reaction time is usually from 1 hour to 2 days, varying based on sorts and volumes of a used starting material and solvent.

For example, the 5-cyano-N-(2-aminophenethyl)-2-hydroxybenzenesulfonamide derivatives represented by the above general formula (II) used as starting materials in the aforementioned production processes can be prepared by the following method:

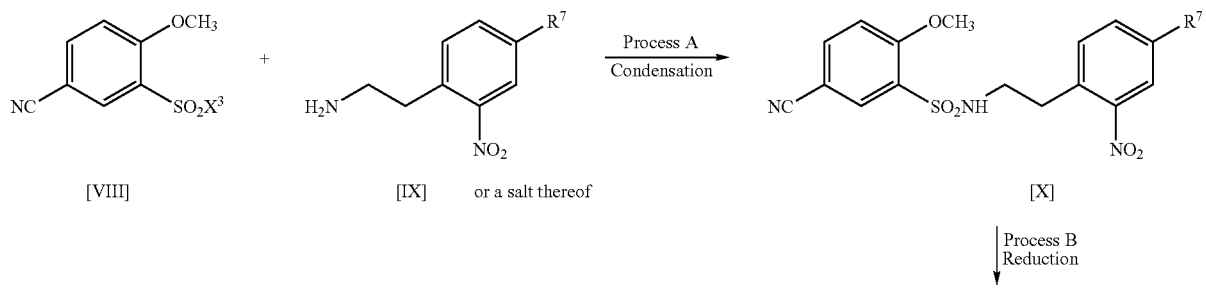

-continued

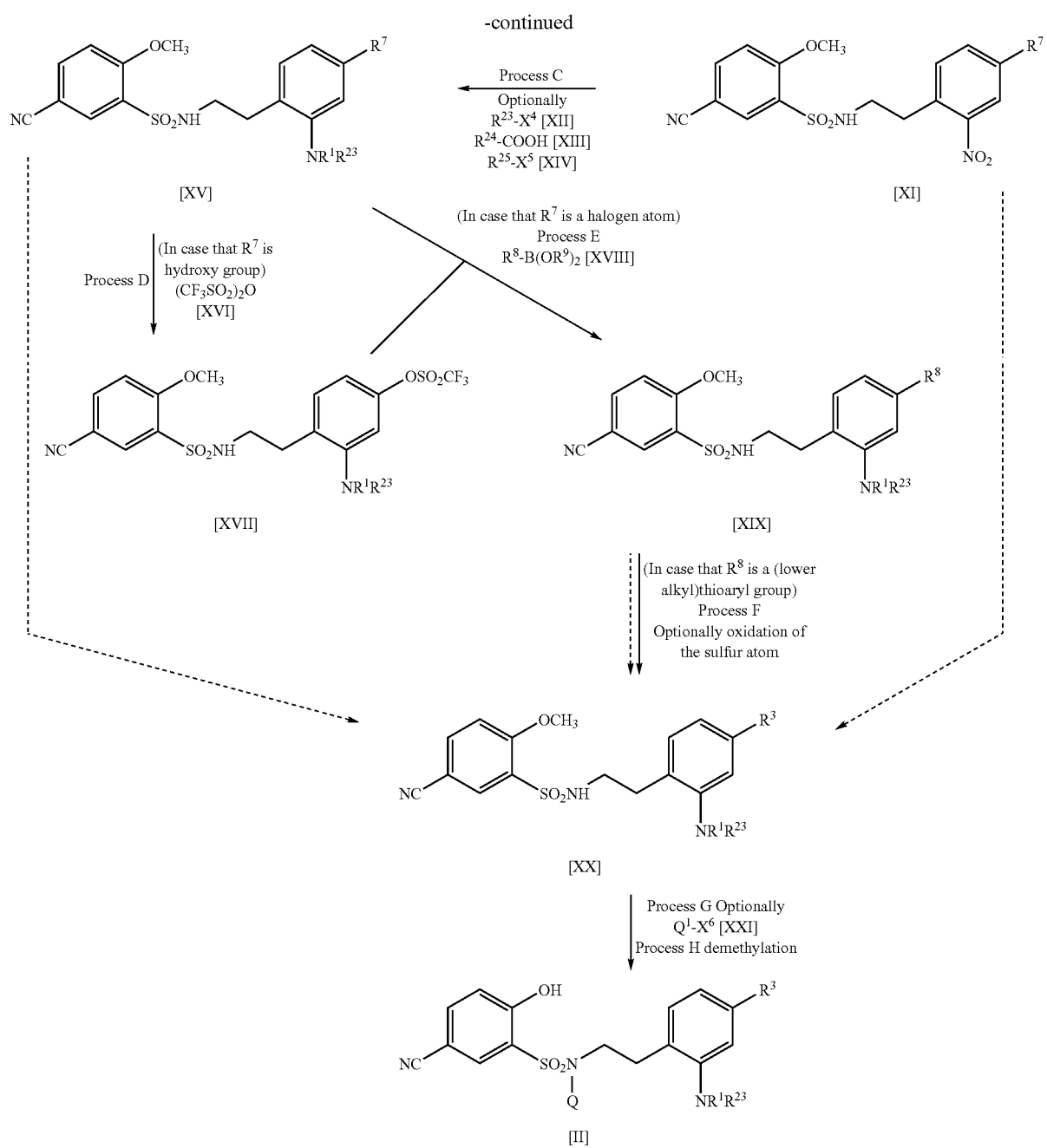

wherein R⁷ represents a halogen atom, a hydroxy group, a di(lower alkyl)amino group, a lower alkyl group, a 3 to 10-membered cycloalkyl group, or a 3 to 10-membered heterocycloalkyl group which may have an oxo group;

R⁸ represents a 6 to 10-membered aryl group which may have one to three substituents selected from the following group (A) or a 5 to 10-membered aromatic heterosyclic group which may have a substituent selected from the following group (B);

(A) an oxo group, a lower alkyl group, a halo(lower alkyl) group, —Y⁵—R^H, a halogen atom, a nitro group, an amino group, —COOR^I, a carbamoyl group, a sufamoyl group, a lower alkylsulfonyl group, a mono(lower alkyl)sulfamoyl group which may have —COOR^J, and a lower alkylsulfonylamino-substituted (lower alkyl) group;
wherein Y⁵, R^H, R^I and R^J have the same meanings as defined above;

(B) a lower alkyl group, an amino group and —COOR^K;
wherein R^K has the same meanings as defined above;

R⁹ represents a hydrogen atom or a lower alkyl group, or both of R⁹ bind to form a lower alkylene group;

R²³ represents a lower alkyl group, —Y¹—COOR^A in which Y¹ and R^A have the same meaning as defined above, —COCOOR^B in which R^B has the same meaning as defined above, —Y²—CONH—R^C in which Y² and R^C have the same meaning as defined above, —COCONH—

$R^D$ in which $R^D$ has the same meaning as defined above, $-CO-Y^3R^E$ in which $Y^3$ and $R^E$ have the same meaning as defined above, $-CO-Y^{41}-R^F$ in which $Y^{41}$ and $R^F$ have the same meaning as defined above, or a lower alkylsulfonylgroup which may have $-COOR^G$ wherein $R^G$ has the same meanings as defined above;

$R^{24}$ represents $-COOR^B$ in which $R^B$ has the same meaning as defined above, $-CONH-R^D$ in which $R^D$ has the same meaning as defined above, $-Y^3-R^E$ in which $Y^3$ and $R^E$ have the same meaning as defined above, or $Y^{41}-R^F$ in which $Y^{41}$ and $R^F$ have the same meaning as defined above;

$R^{25}$ represents a lower alkyl group;

$Q^1$ represents a lower alkyl group which may have a substituent selected from the following group (C);

(C) $-OR^L$, $-COOR^M$, $-CONR^NR^O$, a 6 to 10-membered aryl group which may have one to three substituents selected from the following group (iii), and a 5 to 10-membered aromatic heterocyclic group which may have one to three substituents selected from the following group (iv);

wherein $R^L$, $R^M$, $R^N$ and $R^O$ have the same meanings as defined above;

(iii) a halogen atom, a nitro group, a lower alkyl group, $-OR^P$ in which $R^P$ has the same meaning as defined above, and $-COOR^Q$ in which $R^Q$ has the same meaning as defined above;

(iv) a halogen atom, an oxo group, a lower alkyl group and a phenyl group; and $X^3$ represents a leaving group such as a chlorine atom, a bromine atom or an iodine atom;

$X^4$ to $X^6$ independently represents a leaving group such as a chlorine atom, a bromine atom or an iodine atom, a methanesulofonyloxy group or a p-toluenesulfonyloxy group;

Q, $R^1$ and $R^{22}$ have the same meanings as defined above.

Process A

A benzenesulfonamide derivative represented by the above general formula (X) can be prepared by condensing a benzenesulfonyl halide derivative represented by the above general formula (VIII) with a phenethylamine derivative represented by the above general formula (IX) or a salt thereof in the presence or absence of a base such as triethylamine or potassium carbonate in a polar solvent such as tetrahydrofuran, N,N-dimethylformamide, or a mixed solvent of such solvent with water at usually 0° C. to room temperature.

Process B

An aniline derivative represented by the above general formula (XI) can be prepared by allowing a nitrobenzene derivative represented by the above formula (X) to react with zinc in the presence or absence of an acid such as concentrated hydrochloric acid in a solvent such as acetic acid or water at usually 0° C. to reflux temperature.

Process C

An aniline derivative represented by the above general formula (XI) can be converted into a substituted aniline derivative by allowing it react in accordance with the any method which selected from the following method (1) to (3).

(1) Allowing an aniline derivative represented by the above general formula (XI) to react with a compound represented by the above general formula (XII) in the presence of a base such as potassium carbonate or triethylamine in a solvent such as N,N-dimethylaminopyridine or dichloromethane or the at usually −20° C. to reflux temperature.

(2) Allowing an aniline derivative represented by the above general formula (XI) to react with a compound represented by the above general formula (XII) in the presence of a condensing agent such as 1-(3-dimethylaminopropyl)-3-ethylcarbodiimide hydrochloride or diphenylphosphorylazide, and in the presence or absence of an agent for making an activated ester such as 1-hydroxyybenzotriazole monohydrate, and a base such as triethylamine in a solvent such as N,N-dimethylaminopyridine or dichloromethane at usually −20° C. to reflux temperature.

(3) Allowing an mono-substituted aniline derivative prepared by the above method (1) or (2) to react with a compound represented by the above general formula in the presence of a base such as potassium carbonate or triethylamine in a solvent such as N,N-dimethylaminopyridine or dichloromethane or the at usually −20° C. to reflux temperature.

Process D

A compound represented by the above general formula (XVII) can be prepared by condensing a substituted aniline derivative represented by the above general formula (XI) or (XV) wherein $R^7$ is a hydroxy group with tifluoromethanesulfonic anhydride in the presence of a base such as N,N-dimethylaminopyridine in a solvent such as dichloromethane or tetrahydrofuran at usually 0° C. to room temperature.

Process E

A compound represented by the above general formula (XIX) can be prepared by condensing a compound represented by the above general formula (XVII) or a substituted aniline derivative wherein $R^7$ is a halogen atom represented by the above general formula (VI) with a boron compound represented by the above general formula (XVIII) in the presence of a catalyst such as tetrakis(triphenylphosphine) palladium(0), palladium(II) acetate or [1,1'-bis(diphenylphosphino)ferrocene]chloronickel(II) and a base such as sodium carbonate, sodium hydrogen carbonate, potassium phosphate or triethylamine in the presence or absence of a phase-transfer catalyst such as tetrabutylammonium bromide in a solvent such as toluene, tatrahydrofuran, N,N-dimethylformamide or water, or a mixed solvent thereof at usually room temperature to reflux temperature.

Process F

A compound wherein $R^8$ is a (lower alkyl)thioaryl group represented by the above general formula (XIX) can be converted into a corresponding sulfonyl compound by treating it with an oxidizing agent such as oxone (trademark) or m-chloroperbenzoic acid in a solvent such as acetone or dichloromethane, or a mixed solvent of such solvent with water at usually 0° C. to reflux temperature.

Process G

A corresponding N-alkylated compound can be prepared by subjecting a compound represented by the above general formula (XX) to N-alkylation using an alkylating agent represented by the above general formula (XXI) in the presence of a base such as triethylamine or potassium carbonate in a solvent such as N,N-dimethylformamide at usually −20° C. to reflux temperature.

Process H

A benzenesulfonamide derivative represented by the above general formula (II) can be prepared by subjecting a compound of the above general formula (XX) or a compound N-alkylated by Process G to demethylation under heating in the presence of lithium chloride in a solvent such as N,N-dimethylformamide or N,N-dimethylacetamide at usually 100° C. to reflux temperature.

For example, a compound represented by the above general formula (XX) in the aforementioned production process, a compound wherein $R^{22}$ has an amide group represented by the following general formula (XXa) can be also prepared by the following method:

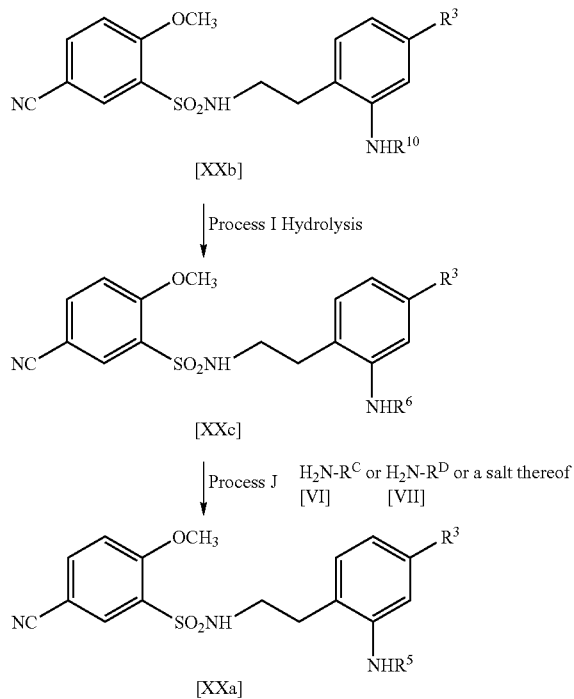

wherein $R^{10}$ represents —$Y^2$—$COOR^{41}$ in which $R^{41}$ is a lower alkyl group or —$COCOOR^{B1}$ in which $R^{B1}$ is a lower alkyl group;

$R^3$, $R^5$, $R^6$, $R^C$, and $R^D$ have the same meanings as defined above.

Process I

A compound represented by the above general formula (XXb) can be hydrolyzed into a corresponding carboxylic acid compound represented by the above general formula (XXc) by treating it with an acid such as hydrochloric acid or sulfuric acid at room temperature to reflux temperature, or with a base such as sodium hydroxide in water, or a mixed solvent of water and acetonitrile, tetrahydrofuran or alcohols and the like at usually 0° C. to reflux temperature.

Process J

A compound represented by the above general formula (XXc) can be converted into a corresponding amide compound represented by the above general formula (XXa) by allowing it to react with an amine compound represented by the above general formula (VI) or a salt thereof, or an amine compound represented by the above general formula (VII) or a salt thereof in the presence of a condensing agent such as 1-(3-dimethylaminoproyl)-3-ethylcarbodiimide hydrochloride or diphenylphoshoryl azide and in the presence or absence of an agent for making an activated ester such as 1-hydroxybenzotriazole monohydrate and a base such as triethylamine in a solvent such as dichloromethane or N,N-dimethylformamide at usually 0° C. to room temperature.

In the aforementioned production process, for example, a compound represented by the above general formula (XIX) can be also prepared by the following method:

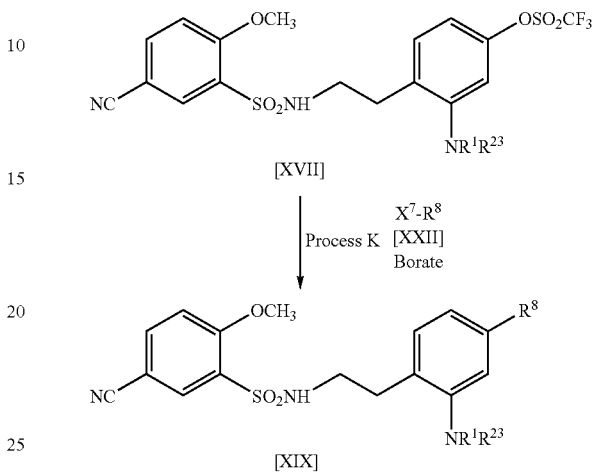

wherein $X^7$ represents a bromine atom, a chlorine atom or an iodine atom; and $R^1$, $R^8$ and $R^{23}$ have the same meanings as defined above.

Process K

A benzenesulfonamide derivative represented by the above general formula (XIX) can be prepared by condensing a benzenesulfonamide derivative represented by the above general formula (XVII) with a halide compound represented by the above general formula (XXII) in the presence of a borate such as bis(pinacolato)diboron and a catalyst such as [1,1'-bis(diphenylphosphino)ferrocene]palladium(II) dichloride dichloromethane complex in a solvent such as dioxane at usually room temperature to reflux temperature.

For example, the compound represented by the above general formula (V) in the aforementioned production process is commercially available or can be prepared by methods described in literature or the like (Michael Folkmann, Synthesis, 1159 (1990); Jose Alxander, J.Med.Chem., 318–322, 31 (1988)).

The compounds of the present invention obtained by the above production process can be easily isolated and purified by conventional separation means such as fractional recrystallization, precipitation, purification using column chromatography, solvent extraction and the like.

The 5-amidino-N-(2-aminophenethyl)-2-hydroxybenzenesulfonamide derivatives represented by the above general formula (I) of the present invention can be converted into their pharmaceutically acceptable salts in the usual way. Examples of the such salts include acid addition salts with mineral acids (e.g., hydrochloric acid, hydrobromic acid, hydroiodic acid, sulfuric acid, nitric acid, phosphoric acid and the like), acid addition salts with organic acids (e.g., formic acid, acetic acid, methanesulfonic acid, benzenesulfonic acid, p-toluenesulfonic acid, propionic acid, citric acid, succinic acid, tartaric acid, fumaric acid, butyric acid, oxalic acid, malonic acid, maleic acid, lactic acid, malic acid, carbonic acid, glutamic acid, aspartic acid and the like), salts with organic amines (e.g., morpholine, pyrrolidine, piperidine, piperazine, lysine and the like), and salts with inorganic bases such as a sodium salt, a potassium salt and a calcium salt.

In addition, the compounds represented by the above general formula (I) of the present invention also include its hydrates and solvates with pharmaceutically acceptable solvents (e.g., ethanol).

Of the compounds represented by the above general formula (I) of the present invention, compounds having an asymmetric carbon atom exist in two optical isomer forms of (R) configuration and (S) configuration. Either one of the isomers or a mixture thereof can be employed in the present invention. In the compounds represented by the above general formula (I) of the present invention, when geometrical isomers or tautomers exist, the present invention includes all of the geometrical isomers and tautomers.

The compounds represented by the above general formula (I) of the present invention are compounds having a potent inhibitory activity on activated blood coagulation factor X and anti-coagulation activity. The compounds represented by the above general formula (I) of the present invention also have an extremely weak inhibitory activity on thrombin and therefore are highly selective activated blood coagulation factor X inhibitors.

Furthermore, among the compounds represented by the above general formula (I) of the present invention, 5-amidino-N-(2-aminophenethyl)-2-hydroxybenzenesulfonamide derivatives represented by the general formula:

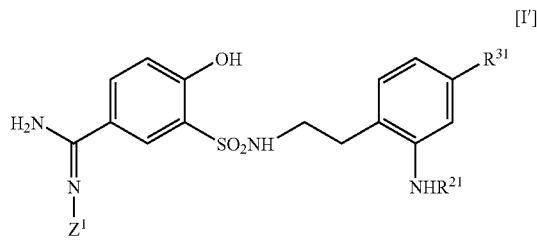

[I']

wherein $R^{21}$ represents $-Y^{11}-COOR^A$ in which $Y^{11}$ is a lower alkylene group; and $R^A$ is a hydrogen atom or a lower alkyl group;

$R^{31}$ represents a 6 to 10-membered aryl group which may have one to three substituents selected from the following group (A);

(A) an oxo group, a lower alkyl group, a halo(lower alkyl)group, $-Y^5-R^H$, a halogen atom, a nitro group, an amino group, $-COOR^I$, a carbamoyl group, a sulfamoyl group, a loweralkylsulfonyl group, a mono(lower alkyl)sulfamoyl group which may have $-COOR^J$, and a loweralkylsulfonylamino-substituted (lower alkyl) group;

wherein $Y^5$ represents an oxygen atom or a sulfur atom;
$R^H$ represents a hydrogen atom, a halo(lower alkyl) group, or a lower alkyl group which may have $-COOR^{H1}$ where $R^{H1}$ is a hydrogen atom, a 3 to 10-membered heterocycloalkyl or a lower alkyl group;

$R^I$ represents a hydrogen atom, a 3 to 10-membered cycloalkyl group or a lower alkyl group;

$R^J$ represents a hydrogen atom, a 3 to 10-membered cycloalkyl group, or lower alkyl group;

$Z^1$ represents a hydroxy group or $-COOR^R$;

wherein $R^R$ is a halo(lower alkyl) group, a 6 to 10-membered aryl group or a lower alkyl group which may have a substituent selected from the following group (ix);

(ix) $-OR^{R1}$ in which $R^{R1}$ is a hydrogen atom or a lower alkyl group, $-COOR^{R2}$ in which $R^{R2}$ is a lower alkyl group which may have $-COOR^{R21}$ where $R^{R21}$ is a lower alkyl group, $-CONR^{R3}R^{R4}$ in which $R^{R3}$ and $R^{R4}$ are independently a hydrogen atom or a lower alkyl group, or $-NR^{R3}R^{R4}$ forms a cyclic amino group, $-OCOR^{R5}$ in which $R^{R5}$ is a lower alkyl group which may have $-OCOR^{R51}$ where $R^{R51}$ is a lower alkyl group, a 3 to 10-membered heterocycloalkyl group and a 6 to 10-membered aryl group;

or pharmaceutically acceptable salts thereof, are specially excellent compounds which also exert an excellent activated blood coagulation factor X inhibitory activity by oral administration.

The compounds represented by the above general formula (I) of the present invention are selective activated blood coagulation factor X inhibitors. In consequence, the compounds of the present invention are extremely useful as agents for the prevention or treatment of cerebral infarction, cerebral thrombosis, cerebral embolism, transient cerebral ischemic attack (TIA), subarachnoid hemorrhage-induced cerebral vasospasm, alzheimer's disease, myocardial infarction, unstable angina, heart failure, thrombosis followed by atrial fibrillation, pulmonary infarction, pulmonary embolism, acute respiratory distress syndrome (ARDS), Berger disease, peripheral arterial obstruction, deep vein thrombosis, disseminated intravascular coagulation syndrome, atherosclerosis, behcet's disease, diabetic neuropathy, diabetic nephropathy, diabetic retinopathy, diabetic thrombotic complications, acute progressive glomerulonephritis, chronic glomerulonephritis, IgA nephropathy, nephritic syndrome, focal segmental glomerulosclreosis, membranous nephropathy, membranoproliferative glomerulonephritis, crescentic glomerulonephritis, lupus nephritis, purpura nephritis, interplanting rejection, systemic inflammatory response syndrome (SIRS), dialysis- or operation-induced thrombocytopenia, thrombus formation after artificial blood vessel operation or after artificial valve replacement, restenosis and reocculusion after coronary intervention such as percutaneous transluminal coronary angioplasty (PTCA) or percutaneous transluminal coronary recanalization (PTCR) surgery and the like, thrombus formation and the like at the time of extracorporeal circulation and the like, agents for the prevention of blood coagulation at the time of insertion of blood vessel catheter, and agents for the prevention or treatment of influenza virus infection based on the activity to inhibit growth of influenza virus.

In addition, the compounds of the present invention can be used suitably in combination with at least one of the drug with the exception of the activated blood coagulation factor X inhibitors. As examples of drugs which can be used in combination with the compound in the present invention, adrenocortical hormone, platelet aggregation inhibitors, adenylate cyclase activators, PGF2α antagonists, cyclooxygenase inhibitors, adenosine antagonists, GPIIb/IIIa antagonists, anticoagulants and fibrinolytic drugs, antithrombin drugs, free-radical scavengers, immunosuppressant drugs, erythropoietin, fish oil, angiotensin-converting enzyme inhibitors, angiotensin II receptor antagonists, glycation inhibitors, protein kinase C inhibitors, aldose reductase inhibitors, endothelin receptor antagonists, endothelin-converting enzyme inhibitors, neutral endopeptidase inhibitors, thromboxane $A_2$ synthetase inhibitors, thromboxane $A_2$ receptor antagonists, $PGI_2$ agonists and the like can be illustrated.

In case of uses of the compound of the above general formula (I) in combination with the one or more drugs selected from the above groups, the present invention includes either dosage forms of a single preparation or separated preparations for simultaneous administration in way of same or different administration route, or dosage forms separated preparation for administration at different administration intervals in way of same or different administration route. A pharmaceutical composition comprising the compound of the above general formula (I) in combination with the above drugs includes both dosage forms as a single preparation and separated preparations for combination as mentioned above.

It can obtain more advantageous effects beyond additive effects in the prevention or treatment of the above diseases by using the compound of the present invention in combination with suitable one or more drugs selected from the above group. And it can be decrease the administration dose in comparison with administration of the compound of the present invention alone, and can be avoided or declined the adverse effects of co-administrated drugs too.

Example compounds as the above drugs used for combination are listed as follows. However, the present invention is not limited thereto, and it also included a compound of free form and pharmaceutically acceptable salts thereof.

As adrenocortical hormone, cortisone acetate, prednisolone, prednisolone sodium succinate, prednisolone sodium phosphate, methylprednisolone, methylprednisolone acetate, triamcinolone, dexamethasone, dexamethasone metasulfobenzoate sodium, dexamethasone sodium phosphate, betamethasone, betamethasone sodium phosphate, prasterone, KSR-592 and the like are illustrated.

As platelet aggregation inhibitors, dilazep dihydrochloride, dipyridamole, cilostazol, alprostadil, iloprost, cloricromene, triflusal, TA-993 and the like are illustrated.

As adenylate cyclase activators, ticlopidine hydrochloride, colforsin daropate hydrochloride, glucagons, PACAP-38 and the like are illustrated.

As PGF2α antagonists, trimetazidine hydrochloride and the like are illustrated.

As cyclooxygenase inhibitors, aspirin, ketoprofen, tiaprofenic acid, alminoprofen, ibuprofen piconol, flurbiprofen, zaltoprofen, pirprofen, tenoxicam, loxoprofen sodium, oxaprozin, suprofen, fenoprofen, tolfenamic acid, pranoprofen, droxicam, amtolmetin guacil, piroxicam succinate, nabmetone, mofezolac, indobufen, lornoxicam, eltenac, ketorolac trometamol, bromfenac sodium hydrate, aceclofenac, diclofenac sodium, cizolirtine citrate, licofelone, S-14080, D-1158, NMI-377, NMI-172, NMI-246, NMI-267, DP-103, MX-1094 and the like are illustrated.

As adenosine antagonists, clopidogrel sulfate, E-3080 and the like are illustrated.

As GPIIb/IIIa antagonists, abciximab, tirofiban hydrochloride, eptifibatide, sibrafiban, roxifiban acetate, gantofiban, cromafiban, elarofiban, YM-337, T-250, DMP-802, UR-3216, YM-68128, HMR-1794, TAK-024, CRL-42796 and the like are illustrated.

As anticogulants, heparin, warfarin and the like are illustrated.

As thrombolitic drugs, urokinase, streptokinase, t-PA(tissue-type plasminogen activator; tisokinase, alteprase, nateplase, monteplase, pamiteplase, nasaruplase and the like) and the like are illustrated.

As antithrombin drugs, hirudin, argatroban, melagatran, ximelagatran, napsagatran, efegatran, CJC-1004, BIBR-1048, TRI-50B, CX-397, LU-57291 and the like are illustrated.

As free-radical scavengers, edaravone and the like are illustrated.

As immunosuppressant drugs, azathioprine, cyclophosphamide, mizoribine, ciclosporin, tacrolimus hydrate, chlorambucil, lobenzarit disodium, auranofin, alprostadil, gusperimus hydrochloride, biosynsorb, muromonab, alefacept, pentostatin, daclizumab, sirolimus, mycophenolate mofetil, leflonomide, basiliximab, dornase α, bindarid, cladribine, pimecrolimus, ilodecakin, cedelizumab, efalizumab, everolimus, anisperimus, gavilimomab, faralimomab, clofarabine, siplizumab, saireito, LDP-03, CD4, SR-43551, SK&F-106615, IDEC-114, IDEC-131, FTY-720, TSK-204, LF-080299, A-86281, A-802715, GVH-313, HMR-1279, ZD-7349, IPL-423323, CBP-1011, MT-1345, CNI-1493, CBP-2011, J-695, LJP-920, L-732531, ABX-RB2, AP-1903, IDPS, BMS-205820, BMS-224818, CTLA4-1g, ER-49890, ER-38925, ISAtx-247, RDP-58, PNU-156804, LJP-1082, TMC-95A, TV-4710, PTR-262-MG, AGI-1096 and the like are illustrated.

As angiotensin-converting enzyme inhibitors, lisinopril, ramipril, fosinopril, enalapril maleate, captopril, alacepril, delapril hydrochloride, benzapril hydrochloride, quinaprilat, imidapril hydrochloride, zofenopril calcium, fosinopril sodium, cilazapril, temocapril hydrochloride, spirapril hydrochloride, quinapril hydrochloride, perindopril erbumine, moexipril hydrochloride, trandolapril, MDL-100240, SA-7060, E-4030, GW-660511 and the like are illustrated.

As angiotensin II receptor antagonists, losartan potassium, valsartan, irbesartan, candesartan cilexetil, eprosartan mesilate, telmisartan, olmesartan, Dup753, PD123177, EXP-3174, EXP-3312, KT-3-671, RU-64276, GA-0113, CS-088 and the like are illustrated.

As glycation inhibitors, pimagedine hydrochloride, ALT-711, EXO-226, KGR-1380, ALT-711 and the like are illustrated.

As protein kinase C inhibitors, midostaurin, perifosine, LY333531, KW-2401, ISIS-3521, ISIS-5132 and the like are illustrated.

As aldose reductase inhibitors, epalrestat, risarestat, fidarestat, tolrestat, zopolrestat, minalrestat, ascorbyl gamolenate, lindolrestat, AD-5467, AS-3201, NZ-314, SG-210, IDD-598, JTT-811 and the like are illustrated.

As endothelin receptor antagonists, bosentan, sitaxsentan sodium, darusentan, atrasentan, tezosentan sodium, ambrisentan, BMS-207940, BMS-193884, S-0139, BQ-610, TA-0201, SB-215355, SB-234551, SB-247083, J-104132, RO-61-1790, PD-180988, LU-302872, TBC-3214, TBC-3711, RPR-118031A, ABT-546, ATZ-1993, YM-598 and the like are illustrated.

As endothelin-converting enzyme inhibitors, SLV-306, CGS-35066, SM-19712 and the like are illustrated.

As neutral endopeptidase inhibitors, omapatrilat, fasidotril, ecadotril, sampatrilat, MDL-100240, SA-7060, SLV-306, E-4030, GW-660511X and the like are illustrated.

As thromboxane $A_2$ synthetase inhibitors, sodium ozagrel, ozagrel hydrochloride, isbogrel, terbogrel, imitrodast sodium, imidazol salicylate, NM-702, S-32080, NIK-639 and the like are illustrated.

As thromboxane $A_2$ receptor antagonists, egualen sodium, seratrodast, ramatroban, epoprostenol sodium, domitroban calcium hydrate, ibudilast, phthalazinol, KT-2-962, Z-335, S-18204, YM-158, S-32080, S-36496, S-35120 and the like are illustrated.

As PGI$_2$ agonists, beraprost sodium, iloprost, clinprost, pimilprost, TY-11223 and the like are illustrated.

When the 5-amidino-N-(2-aminophenethyl)-2-hydroxybenzenesulfonamide derivatives represented by the above general formula (I) of the present invention and pharmaceutically acceptable salts thereof are employed in the practical treatment, they are administered orally or parenterally in the form of appropriate pharmaceutical compositions such as tablets, powders, fine granules, granules, capsules, injections, solutions, adhesive preparations, ointments, inhalants, suppositories and the like. These pharmaceutical compositions can be formulated in accordance with pharmaceutically conventional methods using conventional pharmaceutical carriers, excipients and other additives. In case of the use in combination with the drugs other than the 5-amidino-N-(2-aminophenethyl)-2-hydroxybenzenesulfonamide derivative represented by the above general formula (I), they can be prepared by formulate each active ingredient together or individually.

When the pharmaceutical compositions of the present invention are employed in the practical treatment, the dosage of the 5-amidino-N-(2-aminophenethyl)-2-hydroxybenzenesulfonamide derivatives represented by the above general formula (I) or pharmaceutically acceptable salts thereof is appropriately decided depending on the sex, age, body weight, degrees of symptoms and treatment of each patient, which is approximately within the range of from 1 to 5,000 mg per day per adult human in case of oral administration and approximately within the range of from 0.01 to 500 mg per day per adult human in case of parenteral administration such as injection, and the daily dose can be divided into one to several doses per day. Also, in case of the use in combination with the another drugs, the dosage of the 5-amidino-2-hydroxybenzenesulfonamide derivatives represented by the above general formula (I) or pharmaceutically acceptable salts thereof can be decreased appropriately and occasionally depending on the dosage of the another drugs.

EXAMPLES

The present invention is further illustrated in more detail by way of the following Reference Examples, Examples and Test Examples. However, the present invention is not limited thereto.

Reference Example 1

2-Hydroxyimino-3-(4-isopropyl-2-nitrophenyl)propionic acid

To a stirred suspension of 11.39 g of sodium ethoxide in 100 mL of tetrahydrofuran were added 9.35 mL of 4-isopropyl-1-methyl-2-nitrobenzene and 22.74 mL of diethyl oxalate under ice-cooling. After being stirred at room temperature for 30 minutes, the mixture was refluxed for 20 hours. To the reaction mixture was added 112 mL of 2 mol/L sodium hydroxide solution, and the mixture was stirred at 60° C. for 2 hours. To the reaction mixture were added diethyl ether and water, and the insoluble material was removed by filtration. The filtrate was separated, and the aqueous layer was washed with diethyl ether. To the aqueous layer was added 400 mL of hydrochloric acid, and the mixture was extracted with ethyl acetate. After being washed with water, and brine, the organic layer was dried over anhydrous magnesium sulfate, and the solvent was removed under reduced pressure. To a stirred solution of 3.49 g of the residue in 20 mL of ethanol were added 1.16 g of hydroxylamine hydrochloride and 3.78 mL of pyridine at room temperature, and the mixture was stirred at 70° C. for 2 hours. To the reaction mixture were added 1 mol/L of hydrochloric acid and brine, and the mixture was extracted with ethyl acetate. After being washed with brine, the organic layer was dried over anhydrous magnesium sulfate, and the solvent was removed under reduced pressure to give 2.194 g of 2-hydroxyimino-3-(4-isopropyl-2-nitrophenyl) propionic acid.

$^1$H-NMR (CDCl$_3$) δ ppm: 1.26 (6H, d, J=6.9 Hz), 2.89–3.02 (1H, m), 4.35 (2H, s), 7.20 (1H, d, J=7.9 Hz), 7.36 (1H, dd, J=7.9, 1.6 Hz), 7.81 (1H, d, J=1.6 Hz), 10.70–12.70 (1H, br)

Reference Example 2

(4-Isopropyl-2-nitrophenyl)acetonitrile

To a stirred solution of 1.18 mL of acetic anhydride in 5 mL of acetic acid was added a solution of 2.214 g of 2-hydroxyimino-3-(4-isopropyl-2-nitrophenyl)propionic acid in 5 mL of acetic acid at room temperature, and the mixture was stirred at 50° C. for 2 hours. After the reaction mixture was concentrated under reduced pressure, to the residue were added ethyl acetate and saturated aqueous sodium bicarbonate solution, and the organic layer was separated. The aqueous layer was extracted with ethyl acetate, and the organic layers were combined. After being washed with water, and brine, the organic layer was dried over anhydrous sodium sulfate, and the solvent was removed under reduced pressure to give 1.835 g of (4-isopropyl-2-nitrophenyl)acetonitrile.

$^1$H-NMR (CDCl$_3$) δ ppm: 1.30 (6H, d, J=6.9 Hz), 3.04 (1H, sept, J=6.9 Hz), 4.16 (2H, s), 7.57 (1H, dd, J=7.9, 1.9 Hz), 7.63 (1H, d, J=7.9 Hz), 8.04 (1H, d, J=1.9 Hz)

Reference Example 3

2-(4-Isopropyl-2-nitrophenyl)ethylamine

To a stirred solution of 0.154 g of (4-isopropyl-2-nitrophenyl)acetonitrile in 2 mL of tetrahydrofuran was added 1.62 mL of 0.93 mol/L borane-tetrahydrofuran complex under ice-cooling, and the mixture was stirred at room temperature for 15 hours. The reaction mixture was cooled under ice-cooling, and to the mixture were added 2 mL of methanol and 20 mL of water. After the mixture was extracted with ethyl acetate, the organic layer was washed with brine, and dried over anhydrous magnesium sulfate. The solvent was removed under reduced pressure, and the residue was purified by column chromatography on aminopropylated silica gel (eluent: ethyl acetate) to give 64 mg of 2-(4-isopropyl-2-nitrophenyl)ethylamine.

$^1$H-NMR (CDCl$_3$) δ ppm: 1.24–1.43 (8H, m), 2.92–3.05 (5H, m), 7.29 (1H, d, J=7.9 Hz), 7.40 (1H, dd, J=7.9, 1.9 Hz), 7.76 (1H, d, J=1.9 Hz)

Reference Example 4 tert-Butyl [2-(4-isopropyl-2-nitrophenyl)ethyl]carbamate

To a solution of 64 mg of 2-(4-isopropyl-2-nitro-pheyl) ethylamine in 0.5 mL of tetrahydrofuran was added a solution of 55 mg of di-tert-butyl dicarbonate in 0.5 mL of tetrahydrofuran, and the mixture was stirred at room temperature for 2 hours. The reaction mixture was concentrated under reduced pressure to give 92 mg of tert-butyl [2-(4-isopropyl-2-nitrophenyl)ethyl]carbamate.

$^1$H-NMR (CDCl$_3$) δ ppm: 1.27 (6H, d, J=6.9 Hz), 1.42 (9H, s), 2.87–3.10 (3H, m), 3.35–3.50 (2H, m), 4.73 (1H, br s), 7.26 (1H, d, J=7.9 Hz), 7.40 (1H, dd, J=7.9, 1.6 Hz), 7.73–7.84 (1H, br s)

Reference Example 5 tert-Butyl [2-(2-amino-4-isopropylphenyl)ethyl]carbamate

To a solution of 92 mg of tert-butyl [2-(4-isopropyl-2-nitrophenyl)ethyl]carbamate in 2 mL of ethanol was added 20 mg of 10% palladium-carbon, and the mixture was stirred under hydrogen atmosphere at room temperature for 5 hours. The insoluble was removed by filtration, and the filtrate was concentrated under reduced pressure to give 82 mg of tert-butyl [2-(2-amino-4-isopropylphenyl)ethyl]carbamate.

$^1$H-NMR (CDCl$_3$) δ ppm: 1.22 (6H, d, J=6.9 Hz), 1.55 (9H, s), 2.60–2.86 (3H, m), 3.20–3.40 (2H, m), 4.82 (1H, br s), 6.45–6.60 (2H, m), 6.92 (1H, d, J=7.9 Hz)

Reference Example 6

Ethyl [2-(2-tert-butoxycarbonylaminoethyl)-5-isopropylphenyl]oxalamate

To a stirred solution of 0.15 g of tert-butyl [2-(2-amino-4-isopropylphenyl)ethyl]carbamate and 0.087 mL of pyridine in 2 mL of dichloromethane was added 0.072 mL of ethyl chlorooxoacetate under ice-cooling, and the mixture was stirred at room temperature for 4 hours. To the reaction mixture were added water and ethyl acetate, and the mixture was separated. The aqueous layer was extracted with ethyl acetate, and the organic layers were combined. After being washed with water and brine successively, the organic layer was dried over anhydrous magnesium sulfate, and the solvent was removed under reduced pressure to give 0.23 g of ethyl [2-(2-tert-butoxy-carbonylaminoethyl)-5-isopropylphenyl]oxalamate.

$^1$H-NMR (CDCl$_3$) δ ppm: 1.24 (6H, d, J=6.9 Hz), 1.41 (9H, s), 1.44 (3H, t, J=7.3 Hz), 2.76–2.95 (3H, m), 3.36 (2H, q, J=6.6 Hz), 4.42 (2H, q, J=7.3 Hz), 4.69 (1H, br s), 7.06 (1H, dd, J=7.9, 1.6 Hz), 7.14 (1H, d, J=7.9 Hz), 7.77 (1H, d, J=1.6 Hz), 8.85–9.12 (1H, m)

Reference Example 7

The following compounds were prepared according to a similar manner to that described in Reference Example 6 tert-Butyl [2-(4-isopropyl-2-methanesulfonylaminophenyl)ethyl]carbamate $^1$H-NMR (CDCl$_3$) δ ppm: 1.24 (6H, d, J=6.9 Hz), 1.45 (9H, s), 2.81–2.94 (3H, m), 3.02 (3H, s), 3.17–3.31 (2H, m), 4.79–5.13 (1H, br), 7.02 (1H, d, J=7.9 Hz), 7.10 (1H, d, J=7.9 Hz), 7.39 (1H, s), 7.68–7.93 (1H, br)

Ethyl [[2-(2-tert-butoxycarbonylaminoethyl)-5-isopropylphenyl]sulfamoyl]acetate $^1$H-NMR (CDCl$_3$) δ ppm: 1.23 (6H, d, J=6.9 Hz), 1.26 (3H, t, J=7.3 Hz), 1.44 (9H, s), 2.83–2.97 (3H, m), 3.20–3.35 (2H, m), 4.05 (2H, s), 4.19–4.28 (2H, m), 4.70–4.95 (1H, br), 7.00–7.09 (1H, m), 7.10–7.18 (1H, m), 7.37–7.45 (1H, m), 7.72–7.85 (1H, br)

Reference Example 8

Ethyl [[2-(2-tert-butoxycarbonylaminoethyl)-5-isopropylphenyl](ethyl)sulfamoyl]acetate To a solution of 0.387 g of ethyl [[2-(2-tert-butoxycarbonylaminoethyl)-5-isopropylphenyl]sulfamoyl]acetate in 5 mL of N,N-dimethylformamide were added 0.131 g of potassium carbonate and 0.169 g of ethyl iodide at room temperature, and the mixture was stirred at the same temperature for 2 hours. To the reaction mixture was added water, and the mixture was extracted with ethyl acetate. The organic layer was washed with water and brine, and dried over anhydrous magnesium sulfate. The solvent was removed under reduced pressure, and the residue was purified by column chromatography on silica gel (eluent: ethyl acetate-hexane) to give 0.342 g of ethyl [[2-(2-tert-butoxycarbonylaminoethyl)-5-isopropylphenyl](ethyl)sulfamoyl] acetate.

$^1$H-NMR (CDCl$_3$) δ ppm: 1.09 (3H, t, J=7.3 Hz), 1.25 (6H, d, J=6.9 Hz), 1.36 (3H, t, J=7.3 Hz), 1.42 (9H, s), 2.83–3.05 (3H, m), 3.40–3.50 (2H, m), 3.52–3.63 (1H, m), 3.83–3.93 (1H, m), 3.97 (1H, d, J=13.9 Hz), 4.09 (1H, d, J=13.9 Hz), 4.25–4.38 (2H, m), 4.75–4.90 (1H, br), 7.22 (1H, dd, J=7.9, 1.6 Hz), 7.30–7.37 (2H, m)

Reference Example 9 tert-Butyl [2-[2-[2-(1-ethyl-1H-tetrazol-5-yl)acetylamino]-4-isopropylphenyl]ethyl]carbamate A suspension of 1.0 g of ethyl (1H-tetrazol-5-yl)acetate, 0.566 mL of ethyl iodide and 2.21 g of potassium carbonate in 19 mL of ethyl methyl ketone was stirred in a sealed tube at 95° C. for 3 hours. To the reaction mixture was added water, and the mixture was extracted with ethyl acetate. After being washed with water and brine, the organic layer was dried over anhydrous magnesium sulfate, and the solvent was removed under reduced pressure. The residue was dissolved in 14 mL of ethanol under ice-cooling with stirring, and to the solution was added 2.58 mL of 2 mol/L sodium hydroxide solution. After being stirred at room temperature for 3 hours, the reaction mixture was concentrated under reduced pressure. To the residue was added 2.58 mL of 2 mol/L hydrochloric acid, and the reaction mixture was concentrated under reduced pressure. After being dissolved in ethanol, the residue was dried over anhydrous magnesium sulfate, and the solvent was removed under reduced pressure. To a stirred solution of the residue, 0.33 g of tert-butyl [2-(2-amino-4-isopropylphenyl)ethyl]carbamate and 0.191 g of 1-hydrxybenzotriazole monohydrate in 2.4 mL of N,N-dimethylformamide was added 0.221 g of 1-[3-(dimethylamino)propyl]-3-ethylcarbodiimide hydrochloride under ice-cooling with stirring, and the mixture was stirred at room temperature for 14 hours. To the reaction mixture was added water, and the mixture was extracted with ethyl acetate. The organic layer was washed with water, saturated aqueous sodium bicarbonate solution, and brine, and dried over anhydrous magnesium sulfate. The solvent was removed under reduced pressure, and the residue was purified by column chromatography on silica gel (eluent: ethyl acetate-hexane) to give 0.172 g of tert-butyl [2-[2-[2-(1-ethyl-1H-tetrazol-5-yl)acetylamino]-4-isopropylphenyl] ethyl]carbamate.

¹H-NMR (CDCl₃) δ ppm: 1.22 (6H, d, J=6.9 Hz), 1.47 (9H, s), 1.62 (3H, t, J=7.3 Hz), 2.79–2.92 (3H, m), 3.13–3.25 (2H, m), 4.31 (2H, s), 4.48 (2H, q, J=7.3 Hz), 5.10 (1H, br s), 6.93 (1H, dd, J=7.9, 1.3 Hz), 7.04 (1H, d, J=7.9 Hz), 8.03 (1H, br s), 9.61 (1H, br s)

Reference Example 10

Ethyl N-[2-(2-aminoethyl)-5-isopropylphenyl]oxalamate hydrochloride

To a stirred solution of 0.266 g of ethyl [2-(2-tert-butoxycarbonylaminoethyl)-5-isopropylphenyl]oxalamate in 2 mL of ethanol was added 2 mL of 21% hydrogen chloride-ethanol solution at room temperature. After being stirred at the same temperature for 2 hours, the reaction mixture was concentrated under reduced pressure to give 0.179 g of ethyl N-[2-(2-aminoethyl)-5-isopropylphenyl] oxalamate hydrochloride.

¹H-NMR (CDCl₃) δ ppm: 1.19 (6H, d, J=6.9 Hz), 1.29 (3H, t, J=6.9 Hz), 2.78–2.95 (1H, m), 3.00–3.50 (4H, m), 4.27 (2H, q, J=6.9 Hz), 7.08 (1H, d, J=7.9 Hz), 7.21 (1H, d, J=7.9 Hz), 7.25–7.30 (1H, m), 7.90–8.45 (3H, m), 9.29 (1H, br s)

Reference Example 11

The following compounds were prepared according to a similar manner to that described in Reference Example 10

Ethyl [[2-(2-aminoethyl)-5-isopropylphenyl](ethyl) sulfamoyl]acetate hydrochloride ¹H-NMR (DMSO-d₆) δ ppm: 0.94–1.01 (3H, m), 1.16–1.27 (9H, m), 2.85–3.00 (3H, m), 3.06–3.19 (1H, m), 3.40–3.58 (2H, m), 3.70–3.84 (1H, m), 4.12–4.28 (3H, m), 4.39–4.47 (1H, m), 7.24–7.43 (3H, m), 7.84–8.05 (3H, br)

N-[2-(2-aminoethyl)-5-isopropylphenyl]-2-(1-ethyl-1H-tetrazol-5-yl)acetamide hydrochloride ¹H-NMR (DMSO-d₆) δ ppm: 1.17 (6H, J=6.9 Hz), 1.46 (3H, t, J=7.3 Hz), 2.80–2.91 (3H, m), 2.93–3.03 (2H, m), 4.33 (2H, s), 4.44 (2H, q, J=7.3 Hz), 7.12 (1H, dd, J=7.9, 1.6 Hz), 7.19 (1H, d, J=1.6 Hz), 7.22 (1H, d, J=7.9 Hz), 7.93 (3H, br s), 10.04 (1H, br s)

Reference Example 12

N-[2-(4-Bromophenyl)ethyl]-2,2,2-trifluoroacetamide

To a stirred solution of 0.87 g of 2-(4-bromophenyl) ethylamine and 1.21 mL of triethylamine in 20 mL of dichloromethane was added 0.737 mL of trifluoroacetic anhydride under ice-cooling. After being stirred at the same temperature for an hour, the reaction mixture was poured into a mixture of 100 mL of ethyl acetate, 30 mL of water, and 30 mL of 2 mol/L hydrochloric acid. The organic layer was washed with water, and dried over anhydrous magnesium sulfate. The solvent was removed under reduced pressure, and the residue was recrystallized from ethyl acetate-hexane to give 0.891 g of N-[2-(4-bromophenyl)ethyl]-2,2,2-trifluoroacetamide.

¹H-NMR (CDCl₃) b ppm: 2.85 (2H, t, J=7.0 Hz), 3.56–3.65 (2H, m), 6.27 (1H, br s), 7.04–7.10 (2H, m), 7.43–7.49 (2H, m)

Reference Example 13

N-[2-(4-Bromo-2-nitrophenyl)ethyl]-2,2,2-trifluoroacetamide

To a stirred solution of 23.89 g of N-[2-(4-bromophenyl) ethyl]-2,2,2-trifluoroacetamide in 200 mL of acetonitrile was added in one portion 13.87 g of nitronium tetrafluoroborate under ice-cooling. After the mixture was stirred at room temperature for 15 minutes, to the reaction mixture was added water, and the mixture was extracted with ethyl acetate. The organic layer was washed with brine, and dried over anhydrous magnesium sulfate. The solvent was removed under reduced pressure, and the residue was purified by column chromatography on silica gel (eluent: ethyl acetate-hexane) to give 11.03 g of N-[2-(4-bromo-2-nitrophenyl)ethyl]-2,2,2-trifluoroacetamide.

¹H-NMR (CDCl₃) δ ppm: 3.07–3.21 (2H, m), 3.65–3.78 (2H, m), 6.63–6.86 (1H, br), 7.24–7.31 (1H, m), 7.68–7.76 (1H, m), 8.11–8.17 (1H, m)

Reference Example 14

2-(4-Bromo-2-nitrophenyl)ethylamine

To a solution of 4.856 g of N-[2-(4-bromo-2-nitrophenyl) ethyl]-2,2,2-trifluoroacetamide in 56 mL of methanol was added 3.417 mL of 5 mol/L sodium hydroxide solution. After being stirred at room temperature overnight, and at 50° C. overnight, the reaction mixture was concentrated under reduced pressure. To the residue were added ethyl acetate and water, and the mixture was separated. After the aqueous layer was extracted with ethyl acetate, the organic layers were combined, and washed with brine. After the organic layer was dried over anhydrous magnesium sulfate, the solvent was removed under reduced pressure to give 3.44 g of 2-(4-bromo-2-nitrophenyl)ethylamine.

¹H-NMR (CDCl₃) δ ppm: 2.96–3.05 (4H, br), 7.25–7.31 (1H, m), 7.66 (1H, dd, J=8.2, 2.0 Hz), 8.07 (1H, d, J=2.0 Hz)

Reference Example 15

5-Carbamoyl-2-methoxybenzenesulfonyl chloride

To 1733 g of chlorosulfonic acid was added in small portions 150 g of 4-methoxybenzamide under ice-cooling with stirring during 15 minutes, and the mixture was stirred at room temperature for 14 hours. After being stirred at 50° C. for additional 1.5 hours, the reaction mixture was dropped into 7 kg of ice. The precipitate was collected by filtration, washed with water and hexane to give 230 g of 5-carbamoyl-2-methoxybenzenesulfonyl chloride.

¹H-NMR (DMSO-d₆) δ ppm: 3.81 (3H, s), 7.00 (1H, d, J=8.5 Hz), 7.10 (1H, br s), 7.84 (1H, dd, J=8.5, 2.5 Hz), 7.87 (1H, br s), 8.23 (1H, d, J=2.5 Hz)

Reference Example 16

5-Cyano-2-methoxybenzenesulfonyl chloride

5-Carbamoyl-2-methoxybenzenesulfonyl chloride (150 g) was suspended in 1800 mL of ethyl acetate. After 219 mL of thionyl chloride was dropped to the stirred suspension under ice-cooling, 2.3 mL of N,N-dimethylformamide was added to the mixture. After being stirred at 55° C. for 3 hours, the reaction mixture was concentrated under reduced pressure. To the residue were added ethyl acetate and water, and the separated organic layer was washed with water, saturated aqueous sodium bicarbonate solution, and brine, and dried over anhydrous magnesium sulfate. The solvent was removed under reduced pressure, and the obtained crude product was recrystallized from ethyl acetate-hexane to give 86.8 g of 5-cyano-2-methoxybenzenesulfonyl chloride.

$^1$H-NMR (CDCl$_3$) δ ppm: 4.16 (3H, s), 7.24 (1H, d, J=8.8 Hz), 7.96 (1H, dd, J=8.8, 2.2 Hz), 8.28 (1H, d, J=2.2 Hz)

Reference Example 17

Ethyl N-[2-[2-(5-cyano-2-methoxybenzenesulfonylamino)ethyl]-5-isopropylphenyl]oxalamate To a solution of 0.125 g of ethyl N-[2-(2-aminoethyl)-5-isopropylphenyl]oxalamate in tetrahydrofuran (4 mL)-water (2 mL) were added successively 0.149 g of potassium carbonate and 0.125 g 5-cyano-2-methoxybenzenesulfonyl chloride, and the mixture was stirred at room temperature for 14 hours. To the reaction mixture was added water, and the mixture was extracted with ethyl acetate. The organic layer was washed with water, and brine, and dried over anhydrous sodium sulfate. The solvent was removed under reduced pressure, and the residue was purified by column chromatography on silica gel (eluent: ethyl acetate-hexane) to give 0.21 g of ethyl N-[2-[2-(5-cyano-2-methoxybenzenesulfonylamino)ethyl]-5-isopropylphenyl]oxalamate.

$^1$H-NMR (CDCl$_3$) δ ppm: 1.24 (6H, d, J=6.9 Hz), 1.44 (3H, t, J=7.3 Hz), 2.81 (2H, t, J=6.6 Hz), 2.85–2.96 (1H, m), 3.09–3.26 (2H, m), 3.79 (3H, s), 4.43 (2H, q, J=7.3 Hz), 5.08 (1H, t, J=6.0 Hz), 7.01 (1H, d, J=8.5 Hz), 7.06 (1H, dd, J=7.9, 1.6 Hz), 7.10 (1H, d, J=7.9 Hz), 7.61 (1H, d, J=1.6 Hz), 7.78 (1H, dd, J=8.5, 2.2 Hz), 8.20 (1H, d, J=2.2 Hz), 8.72 (1H, br s)

Reference Example 18

The following compounds were prepared according to a similar manner to that described in Reference Example 17

Ethyl [2-[2-(5-cyano-2-methoxybenzenesulfonylamino)ethyl]-5-isopropylphenyl ](ethyl)sulfamoyl]acetate $^1$H-NMR (CDCl$_3$) δ ppm: 1.01 (3H, t, J=7.3 Hz), 1.25 (6H, d, J=7.3 Hz), 1.37 (3H, t, J=7.3 Hz), 2.73–2.82 (1H, m), 2.85–2.95 (1H, m), 3.01–3.11 (1H, m), 3.17–3.33 (2H, m), 3.43–3.54 (1H, m), 3.82–3.99 (5H, m), 4.07 (1H, d, J=13.6 Hz), 4.28–4.36 (2H, m), 5.33 (1H, t, J=5.7 Hz), 7.03–7.08 (1H, m), 7.19 (1H, dd, J=8.2, 1.9 Hz), 7.22–7.25 (1H, m), 7.33 (1H, d, J=1.9 Hz), 7.79 (1H, dd, J=8.5, 2.2 Hz), 8.21 (1H, d, J=2.2 Hz)

N-[2-(4-Bromo-2-nitrophenyl)ethyl]-5-cyano-2-methoxybenzenesulfonamide $^1$H-NMR (CDCl$_3$) δ ppm: 3.07 (2H, t, J=6.9 Hz), 3.21–3.34 (2H, m), 4.03 (3H, s), 5.09 (1H, t, J=6.4 Hz), 7.10 (1H, d, J=8.7 Hz), 7.30 (1H, d, J=8.2 Hz), 7.68 (1H, dd, J=8.2, 2.1 Hz), 7.83 (1H, dd, J=8.7, 2.2 Hz), 8.07 (1H, d, J=2.1 Hz), 8.17 (1H, d, J=2.2 Hz)

5-Cyano-N-[2-(4-isopropyl-2-nitrophenyl)ethyl]-2-methoxybenzenesulfonamide $^1$H-NMR (CDCl$_3$)δ ppm: 1.27 (6H, d, J=6.9 Hz), 2.97 (1H, sept, J=6.9 Hz), 3.06 (2H, t, J=6.9 Hz), 3.20–3.28 (2H, m), 4.02 (3H, s), 5.09 (1H, t, J=6.0 Hz), 7.10 (1H, d, J=8.8 Hz), 7.30 (1H, d, J=7.9 Hz), 7.44 (1H, dd, J=7.9, 1.9 Hz), 7.78 (1H, d, J=1.9 Hz), 7.82 (1H, dd, J=8.8, 2.2 Hz), 8.20 (1H, d, J=2.2 Hz)

N-[2-[2-(5-Cyano-2-methoxybenzenesulfonylamino)ethyl]-5-isopropylphenyl ]-2-(1-ethyl-1H-tetrazol-5-yl)acetamide $^1$H-NMR (CDCl$_3$) δ ppm: 1.23 (6H, d, J=6.9 Hz), 1.62 (3H, t, J=7.3 Hz), 2.81 (2H, t, J=6.6 Hz), 2.89 (1H, sept, J=6.9 Hz), 3.13 (2H, q, J=6.6 Hz), 3.91 (3H, s), 4.09 (2H, s), 4.47 (2H, q, J=7.3 Hz), 5.75 (1H, t, J=6.6 Hz), 6.99–7.07 (3H, m), 7.60 (1H, d, J=1.6 Hz), 7.80 (1H, dd, J=8.8, 1.9 Hz), 8.18 (1H, d, J=1.9 Hz), 9.15 (1H, br s)

Reference Example 19

5-Cyano-N-[2-(4-isopropyl-2-methanesulfonylaminophenyl)ethyl]-2-methoxybenzenesulfonamide To a solution of 0.205 g of tert-butyl [2-(4-isopropyl-2-methanesulfonylaminophenyl)ethyl]carbamte in 2 mL of ethanol was added 2 mL of 21% hydrogen chloride-ethanol solution at room temperature. After being stirred at room temperature for 2 hours, the reaction mixture was concentrated under reduced pressure. To a solution of the residue in tetrahydrofuran (4 mL)-water (4 mL) were added successively 0.149 g of potassium carbonate and 0.125 g of 5-cyano-2-methoxybenzenesulfonyl chloride, and the mixture was stirred at room temperature for 34 hours. To the reaction mixture was added water, and the mixture was extracted with ethyl acetate. After being washed with water and brine, the organic layer was dried over anhydrous sodium sulfate, and the solvent was removed under reduced pressure to give 0.241 g of 5-cyano-N-[2-(4-isopropyl-2-methanesulfonylaminophenyl)ethyl]-2-methoxybenzenesulfonamide.

$^1$H-NMR (CDCl$_3$) δ ppm: 1.23 (6H, d, J=6.9 Hz), 2.82–2.95 (3H, m), 3.04 (3H, s), 3.13–3.21 (2H, m), 3.96 (3H, s), 5.22–5.39 (1H, br), 6.52 (1H, br s), 7.05–7.16 (3H, m), 7.19 (1H, s), 7.81 (1H, dd, J=8.8, 2.2 Hz), 8.20 (1H, d, J=2.2 Hz)

Reference Example 20

N-[2-(2-Amino-4-bromophenyl)ethyl]-5-cyano-2-methoxybenzenesulfonamide

To a stirred solution of 5.9 g of N-[2-(4-bromo-2-nitrophenyl)ethyl]-5-cyano-2-methoxybenzenesulfonamide and 46 mL of acetic acid in 67 mL of tetrahydrofuran were added successively 2.23 mL of concentrated hydrochloric acid and 8.76 g of zinc under ice-cooling. After the mixture was stirred at room temperature for an hour, and to the reaction mixture was added 25% aqueous ammonia solution to alkalify. After the mixture was extracted with ethyl acetate, the organic layer was washed with brine, and dried over anhydrous magnesium sulfate. The solvent was removed under reduced pressure to give 5.58 g of N-[2-(2-amino-4-bromophenyl)ethyl]-5-cyano-2-methoxybenzenesulfonamide.

$^1$H-NMR (CDCl$_3$) δ ppm: 2.70 (2H, t, J=6.6 Hz), 3.15 (2H, q, J=6.6 Hz), 3.69–3.81 (2H, m), 3.86 (3H, s), 5.06–5.19 (1H, m), 6.75–6.82 (3H, m), 7.03 (1H, d, J=8.8 Hz), 7.81 (1H, dd, J=8.8, 2.2 Hz), 8.17 (1H, d, J=2.2 Hz)

Reference Example 21

The following compound was prepared according to a similar manner to that described in Reference Example 20

N-[2-(2-Amino-4-isopropylphenyl)ethyl]-5-cyano-2-methoxybenzenesulfonamide $^1$H-NMR (CDCl$_3$) δ ppm: 1.20 (6H, d, J=6.9 Hz), 2.72 (2H, t, J=6.6 Hz), 2.79 (1H, sept, J=6.9 Hz), 3.10–3.17 (2H, m), 3.61 (2H, br s), 3.76 (3H, s), 5.16 (1H, t, J=6.0 Hz), 6.55 (1H, d, J=1.6 Hz), 6.60 (1H, dd, J=7.9, 1.6 Hz), 6.85 (1H, d, J=7.9 Hz), 7.00 (1H, d, J=8.5 Hz), 7.79 (1H, dd, J=8.5, 2.2 Hz), 8.20 (1H, d, J=2.2 Hz)

Reference Example 22

Ethyl [5-bromo-2-[2-(5-cyano-2-methoxybenzenesulfonylamino) ethyl]phenylamino]acetate A solution of 12.38 g of N-[2-(2-amino-4-bromo-phenyl)ethyl]-5-cyano-2-methoxybenzenesulfonamide, 3.68 mL of ethyl bromoacetate, and 7.88 mL of N,N-diisopropylethylamine in 100 mL of N,N-dimethylformamide was stirred at 55° C. for 16 hours. To the reaction mixture was added water, and the mixture was extracted with ethyl acetate. The organic layer was washed with water, and brine, and dried over anhydrous magnesium sulfate. The solvent was removed under reduced pressure, and the residue was purified by column chromatography on silica gel (eluent: ethyl acetate-hexane) to give 7.38 g of ethyl [5-bromo-2-[2-(5-cyano-2-methoxybenzenesulfonylamino) ethyl]phenylamino]acetate.

$^1$H-NMR (CDCl$_3$) δ ppm: 1.32 (3H, t, J=7.3 Hz), 2.75 (2H, t, J=6.6 Hz), 3.15–3.23 (2H, m), 3.85 (2H, d, J=5.4 Hz), 3.86 (3H, s), 4.28 (2H, q, J=7.3 Hz), 4.41 (1H, t, J=5.4 Hz), 5.11 (1H, t, J=6.0 Hz), 6.57 (1H, s), 6.79–6.82 (2H, m), 7.02 (1H, d, J=8.8 Hz), 7.80 (1H, dd, J=8.8, 1.9 Hz), 8.22 (1H, d, J=1.9 Hz)

Reference Example 23

The following compound was prepared according to a similar manner to that described in Reference Example 22

Ethyl [2-[2-(5-cyano-2-methoxybezenesulfonylamino)ethyl]-5-isopropylphenylamino]acetate $^1$H-NMR (CDCl$_3$) δ ppm: 1.21 (6H, d, J=6.9 Hz), 1.31 (3H, t, J=7.0 Hz), 2.72–2.87 (3H, m), 3.14–3.22 (2H, m), 3.78 (3H, s), 3.89 (2H, d, J=5.4 Hz), 4.26 (2H, q, J=7.0 Hz), 5.15 (1H, t, J=6.0 Hz), 6.34 (1H, d, J=1.6 Hz), 6.59 (1H, dd, J=7.6, 1.6 Hz), 6.88 (1H, d, J=7.6 Hz), 7.00 (1H, d, J=8.5 Hz), 7.78 (1H, dd, J=8.5, 2.2 Hz), 8.23 (1H, d, J=2.2 Hz)

Reference Example 24

Ethyl (1-trityl-1H-tetrazol-5-yl)acetate

To a stirred suspension of 0.969 g of ethyl (1H-tetrazol-5-yl)acetate in 9mL of tetrahydrofuran were added successively 0.932 mL of triethylamine and 1.68 g of trityl chloride at room temperature, and the mixture was stirred at the same temperature for 2 hours. To the reaction mixture was added water, and the mixture was extracted with ethyl acetate. The organic layer was washed with water, and 1 mol/L hydrochloric acid, and dried over anhydrous magnesium sulfate. The solvent was removed under reduced pressure, and the residue was purified by column chromatography on silica gel (eluent: ethyl acetate-hexane) to give 1.23 g of ethyl (1-trityl-1H-tetrazol-5-yl)acetate.

$^1$H-NMR (CDCl$_3$) δ ppm: 1.23 (3H, t, J=7.3 Hz), 4.01 (2H, s), 4.17 (2H, q, J=7.3 Hz), 7.08–7.14 (6H, m), 7.28–7.39 (9H, m)

Reference Example 25

(1-Trityl-1H-tetrazol-5-yl)acetic acid

To a stirred solution of 1.21 g of ethyl (1-trityl-1H-tetrazol-5-yl)acetate in ethanol (6mL)-tetrahydrofuran (6 mL) was added 1.67 mL of 2 mol/L sodium hydroxide solution under ice-cooling, and the mixture was stirred at room temperature for an hour. To the reaction mixture were added ethyl acetate and 10 mL of 1 mol/L hydrochloric acid, and the mixture was separated. After being washed with water, and brine, the organic layer was dried over anhydrous magnesium sulfate, and the solvent was removed under reduced pressure to give 1.32 g of (1-trityl-1H-tetrazol-5-yl)acetic acid.

$^1$H-NMR (DMSO-d$_6$) δ ppm: 4.01 (2H, s), 6.97–7.05 (6H, m), 7.36–7.45 (9H, m), 12.84 (1H, br s)

Reference Example 26

2,2-Dimethyl-1,3-dioxolane-4,5-dicarboxylic acid monomethyl ester

To a stirred solution of 1.23 mL of dimethyl 2,2-dimethyl-1,3-dioxolane-4,5-dicarboxylate in 12 mL of methanol was added slowly 3.0 mL of 2 mol/L sodium hydroxide solution under ice-cooling. After being stirred at room temperature for 24 hours, the reaction mixture was concentrated under reduced pressure, and the residue was diluted with 15 ml of water. After the mixture was washed with diethyl ether, acidified by addition of 4 mL of 2 mol/L hydrochloric acid. After the aqueous layer was extracted with dichloromethane, the organic layer was washed with brine, and dried over anhydrous magnesium sulfate. The solvent was removed under reduced pressure to give 0.686 g of 2,2-dimethyl-1,3-dioxolane-4,5-dicarboxylic acid monomethyl ester.

$^1$H-NMR (CDCl$_3$) δ ppm: 1.51 (3H, s), 1.53 (3H, s), 3.85 (3H, s), 4.82 (1H, d, J=5.4 Hz), 4.89 (1H, d, J=5.4 Hz), 7.00–9.70 (1H, br)

Reference Example 27

N-[2-[2-(5-Cyano-2-methoxybenzenesulfonylamino) ethyl]-5-isopropylphenyl]-2-(1-trityl-1H-tetrazol-5-yl)acetamide To a stirred solution of 0.30 g of N-[2-(2-amino-4-isopropylphenyl)ethyl]-5-cyano-2-methoxybezenesulfonamide, 0.298 g of (1-trityl-1H-tetrazol-5-yl)acetic acid and 0.129 g of 1-hydroxybenzotriazole monohydrate in 2.4 mL of N,N-dimethylformamide was added 0.140 g of 1-[3-(dimethylamino)propyl]-3-ethylcarbodiimide hydrochloride under ice-cooling, and the mixture was stirred at room temperature for 14 hours. To the reaction mixture was added water, and the mixture was extracted with ethyl acetate. The organic layer was washed with 1 mol/L hydrochloric acid, water, and brine, and dried over anhydrous magnesium sulfate. The solvent was removed under reduced pressure, and the residue was purified by column chromatography on silica gel (eluent: ethyl acetate-hexane) to give 0.549 g of N-[2-[2-(5-cyano-2-methoxybenzenesulfonylamino)ethyl]-5-isopropylphenyl]-2-(1-trityl-1H-tetrazol-5-yl)acetamide.

$^1$H-NMR (CDCl$_3$) δ ppm: 1.22 (6H, d, J=6.9 Hz), 2.66 (2H, t, J=6.6 Hz), 2.80–2.91 (1H, m), 3.04–3.11 (2H, m), 3.63 (3H, s), 4.08 (2H, s), 6.91 (1H, d, J=8.8 Hz), 6.96–7.03 (2H, m), 7.07–7.13 (6H, m), 7.29–7.42 (10H, m), 7.72 (1H, dd, J=8.8, 2.2 Hz), 7.75–7.84 (1H, m), 8.14 (1H, d, J=2.2 Hz), 8.58 (1H, s)

Reference Example 28

The following compound was prepared according to a similar manner to that described in Reference Example 27

Methyl 5-[[2-[2-(5-cyano-2-methoxybenzenesulfonylamino)ethyl]-5-isopropylphenyl]carbamoyl]-2,2-dimethyl-1,3-dioxolane-4-carboxylate $^1$H-NMR (CDCl$_3$) δ ppm: 1.24 (6H, d, J=6.9 Hz), 1.53 (3H, s), 1.57 (3H, s), 2.80 (2H, t, J=6.3 Hz), 2.89 (1H, sept, J=6.9 Hz), 3.13 (2H, q, J=6.3 Hz), 3.73 (3H, s), 3.88 (3H, s), 4.73 (1H, d, J=5.5 Hz), 4.86 (1H, d, J=5.5 Hz), 5.11 (1H, t, J=6.3 Hz), 6.99 (1H, d, J=8.6 Hz), 7.03–7.06 (2H, m), 7.54–7.58 (1H, m), 7.77–7.82 (1H, m), 8.15–8.23 (2H, m)

Reference Example 29

2-Bromophenyl(methyl)sulfone

To a solution of 2.0 g of 2-bromophenyl(methyl)sulfide in 50 mL of dichloromethane was added 4.28 g of 3-chloroperoxybenzoic acid at room temperature, and the mixture was stirred at the same temperature for 18 hours. To the reaction mixture was added 150 mL of 20% aqueous sodium hydrogen sulfite solution, and the mixture was extracted with ethyl acetate. After being washed with aqueous sodium bicarbonate solution, and brine, the organic layer was dried over anhydrous magnesium sulfate, and the solvent was removed under reduced pressure to give 2.25 g of 2-bromophenyl (methyl)sulfone.

$^1$H-NMR (CDCl$_3$) δ ppm: 3.30 (3H, s), 7.49 (1H, td, J=7.3, 1.9 Hz), 7.54 (1H, td, J=7.3, 1.6 Hz), 7.78 (1H, dd, J=7.3, 1.6 Hz), 8.20 (1H, dd, J=7.3, 1.9 Hz)

Reference Example 30

Ethyl [[4-[2-(5-cyano-2-methoxybenzenesulfonylamino)ethyl]-2'-methanesulfonylbiphenyl-3-yl]amino]acetate A suspension of 0.20 g of ethyl [5-bromo-2-[2-(5-cyano-2-methoxybenzenesulfonylamino)ethyl]phenylamino]acetate, 0.113 g of 4,4,5,5,4',4',5',5'-octamethyl-2,2'-bi[[1,3,2] dioxaborolanyl], 8.8 mg of [bis(diphenylphosphino) ferrocene]dichloropalladium(II), 6.7 mg of bis (diphenylphosphino) ferrocene, and 0.118 g of potassium acetate in 3.2 mL of 1,4-dioxane was stirred under argon atmosphere at 80° C. for 20 hours. To the reaction mixture were added 94.7 mg of 2-bromophenyl(methyl)sulfone, 8.8 mg of [bis(diphenylphosphino)ferrocene]dichloropalladium (II), 257 mg of potassium phosphate, and 0.5 mL of 1,4-dioxane. After being stirred under argon atmosphere at 80° C. for 36 hours, the reaction mixture was diluted successively with ethyl acetate and water, and filtered through a diatomaceous earth column pretreated by water. The organic layer was concentrated under reduced pressure, and the residue was purified by column chromatography on silica gel (eluent: ethyl acetate-hexane) to give 0.145 g of ethyl [[4-[2-(5-cyano-2-methoxybenzenesulfonylamino)ethyl]-2'-methanesulfonylbiphenyl-3-yl]amino]acetate.

$^1$H-NMR (CDCl$_3$) δ ppm: 1.26 (3H, t, J=7.3 Hz), 2.62 (3H, s), 2.86 (2H, t, J=6.9 Hz), 3.20–3.30 (2H, m), 3.90–4.00 (5H, m), 4.23 (2H, q, J=7.3 Hz), 4.47 (1H, t, J=5.7 Hz), 5.28 (1H, t, J=6.3 Hz), 6.70–6.80 (2H, m), 7.00–7.15 (2H, m), 7.30–7.40 (1H, m), 7.50–7.65 (2H, m), 7.80–7.85 (1H, m), 8.20–8.30 (2H, m)

Example 1

N-[2-[2-(5-Cyano-2-hydroxybenzenesulfonylamino) ethyl]-5-isopropylphenyl]oxalamic acid (Compound 1)

To a solution of 0.21 g of ethyl N-[2-[2-(5-cyano-2-methoxybenzenesulfonylamino)ethyl]-5-isopropylphenyl] oxalamate in 3 mL of N,N-dimethylformamide was added 56 mg of lithium chloride, and the mixture was stirred at 140° C. for 4 hours. To the reaction mixture was added 1 mol/L hydrochloric acid, and the mixture was extracted with ethyl acetate. After the organic layer was dried over anhydrous sodium sulfate, the solvent was removed under reduced pressure to give 0.198 g of N-[2-[2-(5-cyano-2-hydroxybenzenesulfonylamino)ethyl]-5-isopropylphenyl] oxalamic acid.

$^1$H-NMR (CDCl$_3$) δ ppm: 1.22 (6H, d, J=6.9 Hz), 2.72–2.95 (3H, m), 3.17–3.36 (2H, m), 6.04–6.24 (1H, br), 6.97–7.14 (3H, m), 7.40–7.46 (1H, m), 7.61 (1H, dd, J=8.5, 1.9 Hz), 7.97 (1H, d, J=1.9 Hz), 9.06 (1H, br s)

Example 2

The following compounds were prepared according to a similar manner to that described in Example 1

5-Cyano-2-hydroxy-N-[2-(4-isopropyl-2-methanesulfonylaminophenyl)ethyl]benzenesulfonamide (Compound 2)

$^1$H-NMR (CDCl$_3$) δ ppm: 1.23 (6H, d, J=6.9 Hz), 2.84–2.92 (1H, m), 2.95 (2H, t, J=6.9 Hz), 3.06 (3H, s), 3.28 (2H, t, J=6.9 Hz), 5.88–6.15 (1H, br), 6.81–7.15 (4H, m), 7.18 (1H, d, J=1.6 Hz), 7.62 (1H, dd, J=8.8, 2.2 Hz), 7.95 (1H, d, J=2.2 Hz)

Ethyl [[2-[2-(5-cyano-2-hydroxybenzenesulfonylamino)ethyl]-5-isopropylphenyl ](ethyl)sulfamoyl] acetate (Compound 3)

$^1$H-NMR (CDCl$_3$) δ ppm: 1.18–1.29 (9H, m), 1.30–1.38 (3H, m), 2.72–2.87 (3H, m), 3.27–3.35 (2H, m), 3.97 (2H, s), 4.05–4.35 (4H, m), 5.81 (1H, br s), 6.36–6.40 (1H, m), 6.59–6.63 (1H, m), 6.85–6.89 (1H, m), 7.01–7.06 (1H, m), 7.62–7.67 (1H, m), 7.93–7.97 (1H, m), 8.80–9.75 (1H, br)

Ethyl [[4-[2-(5-cyano-2-hydroxybenzenesulfonylamino)ethyl]-2'-methanesulfonylbiphenyl-3-yl] amino]acetate (Compound 4)

$^1$H-NMR (DMSO-d$_6$) δ ppm: 1.11 (3H, t, J=7.3 Hz), 2.65–2.75 (5H, m), 3.00–3.15 (2H, br), 3.90–3.95 (2H, m), 4.05 (2H, q, J=7.3 Hz), 5.40–5.45 (1H, m), 6.45–6.50 (1H, m), 6.55–6.65 (1H, m), 7.02 (1H, d, J=7.6 Hz), 7.10–7.50 (4H, m), 7.60–7.75 (2H, m), 7.85–7.90 (1H, m), 8.00–8.10 (2H, m)

Ethyl [[2-[2-(5-cyano-2-hydroxybenzenesulfony-
lamino)ethyl]-5-isopropylphenyl]amino]acetate
(Compound 5)

$^1$H-NMR (CDCl$_3$) δ ppm: 1.21 (6H, d, J=6.9 Hz), 1.33 (3H, t, J=7.3 Hz), 2.73–2.87 (3H, m), 3.28–3.36 (2H, m), 3.98 (2H, s), 4.29 (2H, q, J=7.3 Hz), 5.75–5.85 (1H, m), 6.39 (1H, d, J=1.6 Hz), 6.61 (1H, dd, J=7.6, 1.6 Hz), 6.87 (1H, d, J=7.6 Hz), 7.04 (1H, d, J=8.8 Hz), 7.65 (1H, dd, J=8.8, 2.2 Hz), 7.95 (1H, d, 2.2 Hz), 9.00–9.50 (1H, br)

Methyl 5-[[2-[2-(5-cyano-2-hydroxybenzenesulfo-
nylamino)ethyl]-5-isopropylphenyl]carbamoyl]-2,2-
dimethyl-1,3-dioxolane-4-carboxylate (Compound 6)

$^1$H-NMR (CDCl$_3$) δ ppm: 1.25 (6H, d, J=6.9 Hz), 1.61 (3H, s), 1.62 (3H, s), 2.36 (3H, s), 2.70–2.96 (3H, m), 3.23–3.30 (2H, m), 4.77 (1H, d, J=7.9 Hz), 4.83 (1H, d, J=7.9 Hz), 5.59 (1H, t, J=5.7 Hz), 7.07 (1H, d, J=8.8 Hz), 7.10–7.20 (3H, m), 7.30 (1H, d, J=1.6 Hz), 7.66 (1H, dd, J=8.8, 1.9 Hz), 7.92 (1H, d, J=1.9 Hz), 8.39 (1H, br s)

Example 3

[[2-[2-(5-Cyano-2-hydroxybenzenesulfonylamino)
ethyl]-5-isopropylphenyl]amino]acetic acid (Com-
pound 7)

To a solution of 1.65 g of ethyl [[2-[2-(5-cyano-2-hydroxybenzenesulfonylamino)ethyl]-5-isopropylphenyl] amino]acetate in 10 mL of ethanol was added 14 mL of 2 mol/L sodium hydroxide solution at room temperature, and the mixture was stirred at the same temperature for 3 hours. To the reaction mixture was added 15 mL of 2 mL of hydrochloric acid, and the mixture was extracted with ethyl acetate. The organic layer was washed with brine, and dried over anhydrous sodium sulfate. The solvent was removed under reduced pressure to give 1.416 g of [[2-[2-(5-cyano-2-hydroxybenzenesulfonylamino)ethyl]-5-isopropylphenyl] amino]acetic acid.

$^1$H-NMR (CDCl$_3$) δ ppm: 1.21 (6H, d, J=6.9 Hz), 2.73–2.88 (3H, m), 3.27 (2H, t, J=6.6 Hz), 4.04 (2H, s), 6.46 (1H, s), 6.89 (1H, d, J=7.9 Hz), 7.01–7.07 (1H, m), 7.63 (1H, dd, J=8.5, 1.9 Hz), 7.96 (1H, d, J=1.9 Hz)

Example 4

Ethyl 3-[2-[[2-[2-(5-cyano-2-hydroxybenzenesulfo-
nylamino)ethyl]-5-isopropylphenyl]amino]acety-
lamino]propionate (Compound 8)

To a stirred solution of 0.11 g of ethyl 3-aminopropionate hydrochloride in 10 mL of N,N-dimethylformamide were added 0.072 ml of triethylamine, 0.30 g of [[2-[2-(5-cyano-2-hydroxybenzenesulfonylamino)ethyl]-5-isopropylphenyl] amino]acetic acid, and 0.121 g of 1-hydroxybenzotriazole monohydrate under ice-cooling, and the mixture was stirred at 5minutes. To the mixture was added 0.140 g of 1-[3-(dimethylamino)propyl]-3-ethylcarbodiimide hydrochloride under the same condition, and the mixture was stirred at room temperature for 7 hours. To the reaction mixture was added 1 mol/L hydrochloric acid, and the mixture was extracted with ethyl acetate. The organic layer was washed with water and brine, and dried over anhydrous magnesium sulfate. The solvent was removed under reduced pressure, and the residue was purified by column chromatography on silica gel (eluent: ethyl acetate-hexane) to give 0.278 g of ethyl 3-[2-[[2-[2-(5-cyano-2-hydroxybenzenesulfony-lamino)ethyl]-5-isopropylphenyl]amino]acetylamino]propionate.

$^1$H-NMR (DMSO-d$_6$) δ ppm: 1.05 (3H, t, J=7.3 Hz), 1.11 (6H, d, J=6.9 Hz), 2.41 (2H, t, J=6.6 Hz), 2.57–2.62 (2H, m), 2.65–2.74 (1H, m), 2.95–3.04 (2H, m), 3.40–3.48 (2H, m), 3.63 (2H, s), 3.99 (2H, q, J=7.3 Hz), 4.32–4.40 (1H, br), 5.12–5.36 (1H, br), 6.16 (1H, d, J=1.6 Hz), 6.42 (1H, dd, J=7.6, 1.6 Hz), 6.80 (1H, d, J=7.6 Hz), 7.85 (1H, dd, J=8.5, 2.2 Hz), 7.91–7.96 (1H, m), 7.99 (1H, d, J=8.5 Hz), 8.01 (1H, d, J=2.2 Hz), 11.60–12.60 (1H, br)

Example 5

Ethyl [[[2-[2-(5-cyano-2-hydroxybenzenesulfony-
lamino)ethyl]-5-isopropylphenyl]aminooxalyl]
amino]acetate (Compound 9)

To a solution of 0.333 g of N-[2-[2-(5-cyano-2-hydroxybenzenesulfonylamino)ethyl]-5-isopropylphenyl]oxalamic acid, 0.118 g of ethyl aminoacetate hydrochloride, and 0.13 g of 1-hydroxybenzotriazole monohydrate in 5 mL of N,N-dimethylformamide were added successively 0.118 mL of triethylamine and 0.163 g of 1-[3-(dimethylamino)propyl]-3-ethylcarbodiimide hydrochloride at room temperature, and the mixture was stirred at the same temperature for 16 hours. To the reaction mixture was added water, and the mixture was extracted with ethyl acetate. After being washed with saturated aqueous sodium bicarbonate solution, and brine, the organic layer was dried over anhydrous sodium sulfate. The solvent was removed under reduced pressure, and the reisdue was purified by column chromatography on silica gel (eluent: ethyl acetate-hexane) to give 0.254 g of ethyl [[[2-[2-(5-cyano-2-hydroxybenzenesulfonylamino) ethyl]-5-isopropylphenyl]aminooxalyl]amino]acetate.

$^1$H-NMR (CDCl$_3$) δ ppm: 1.22 (6H, d, J=6.9 Hz), 1.33 (3H, t, J=7.3 Hz), 2.75 (2H, t, J=6.6 Hz), 2.88 (1H, sept, J=6.9 Hz), 3.26 (2H, t, J=6.6 Hz), 4.17 (2H, d, J=6.3 Hz), 4.28 (2H, q, J=7.3 Hz), 5.95 (1H, br s), 7.04 (1H, d, J=8.5 Hz), 7.07 (2H, s), 7.35 (1H, s), 7.63 (1H, dd, J=8.5, 2.2 Hz), 7.95 (1H, d, J=2.2 Hz), 8.06–8.13 (1H, m), 9.08 (1H, br s)

Reference Example 31

Hydroxylammonium acetate

To 100 mL of 50% aqueous hydroxylamine solution was added slowly 86.6 mL of acetic acid under ice-cooling with stirring, and the mixture was stirred at the same temperature for 40 minutes, then at room temperature for 40 minutes. After the reaction mixture was concentrated under reduced pressure, the residue was dissolved in 50 mL of ethanol, and the solution was concentrated under reduced pressure. To the residue was added toluene, and the mixture was concentrated under reduced pressure, and dried to give 76.4 g of hydroxylammonium acetate.

$^1$H-NMR (DMSO-d$_6$) δ ppm: 1.88 (3H, s), 7.63 (4H, br s)

Example 6

Ethyl 3-[2-[[2-[2-(5-carbamimidoyl-2-hydroxyben-
zenesulfonylamino)ethyl]-5-isopropylphenyl]amino]
acetylamino]propionate (Compound 10)

Ethyl 3-[2-[[2-[2-(5-cyano-2-hydroxybenzenesulfony-
lamino)ethyl]-5-isopropylphenyl]amino]acetylamino]propionate (0.278 g) was dissolved in 10.0 mL of 39% hydrogen chloride-ethanol solution, and the solution was stirred at room temperature for 4 hours. The reaction mixture was concentrated under reduced pressure, and the residue was dissolved in 1.0 mL of ethanol. To the solution was added 249 mg of ammonium acetate, and the mixture was stirred at room temperature for 20 hours. The reaction mixture was concentrated under reduced pressure, and to the residue were added water and hexane. The precipitate was collected by filtration to give 0.219 g of ethyl 3-[2-[[2-[2-(5-carbamimidoyl-2-hydroxybenzenesulfonylamino)ethyl]-5-isopropylphenyl]amino]acetylamino]propionate.

$^1$H-NMR (DMSO-$d_6$) δ ppm: 0.91–1.40 (9H, m), 2.73–3.00 (2H, m), 3.03–3.73 (6H, m), 3.80–4.34 (2H, m), 6.06–6.58 (2H, m), 6.63–7.75 (3H, m), 7.80–8.40 (3H, m), 8.47–8.90 (2H, br)

Example 7

The following compounds were prepared according to a similar manner to that described in Example 6

Ethyl [[[2-[2-(5-carbamimidoyl-2-hydroxybenzenesulfonylamino)ethyl]-5-isopropylphenyl]aminooxalyl]amino]acetate (Compound 11)

$^1$H-NMR (DMSO-$d_6$) δ ppm: 1.20 (6H, d, J=6.9 Hz), 1.25 (3H, t, J=7.3 Hz), 2.60–2.70 (2H, m), 2.75–2.90 (3H, m), 3.95 (2H, d, J=6.0 Hz), 4.15 (2H, q, J=7.3 Hz), 6.25–6.40 (1H, m), 6.90 (1H, br s), 7.05–7.25 (3H, m), 7.45–7.55 (1H, m), 7.75–8.05 (3H, m), 8.50 (2H, br s), 9.25–9.30 (1H, m), 10.15 (1H, br s)

5-Carbamimidoyl-2-hydroxy-N-[2-(4-isopropyl-2-methanesulfonylaminophenyl)ethyl]benzenesulfonamide (Compound 12)

$^1$H-NMR (DMSO-$d_6$) δ ppm: 1.17 (6H, d, J=6.9 Hz), 2.73–2.79 (2H, m), 2.80-2.90 (3H, m), 2.92 (3H, s), 6.32 (1H, d, J=9.1 Hz), 7.05 (1H, dd, J=7.9, 1.6 Hz), 7.13 (1H, d, J=7.9 Hz), 7.15 (1H, d, J=1.6 Hz), 7.51 (1H, dd, J=9.1, 2.8 Hz), 7.60–8.80 (7H, m)

Ethyl [[4-[2-(5-carbamimidoyl-2-hydroxybenzenesulfonylamino)ethyl]-2'-methanesulfonylbiphenyl-3-yl]amino]acetate (Compound 13)

$^1$H-NMR (DMSO-$d_6$) δ ppm: 1.08 (3H, t, J=7.1 Hz), 2.60–2.75 (5H, m), 2.80–2.95 (2H, m), 3.85–3.95 (2H, m), 4.01 (2H, q, J=7.1 Hz), 5.65–5.75 (1H, m), 6.28 (1H, d, J=9.2 Hz), 6.43 (1H, s), 6.58 (1H, d, J=7.5 Hz), 6.85–6.95 (1H, m), 6.99 (1H, d, J=7.5 Hz), 7.35 (1H, d, J=7.5 Hz), 7.45–7.90 (5H, m), 7.95–8.10 (2H, m), 8.45–8.60 (2H, br)

Ethyl [[2-[2-(5-carbamimidoyl-2-hydroxybenzenesulfonylamino)ethyl]-5-isopropylphenyl]amino]acetate (Compound 14)

$^1$H-NMR (DMSO-$d_6$) δ ppm: 1.11 (6H, d, J=6.9 Hz), 1.15 (3H, t, J=6.9 Hz), 2.54–2.61 (2H, m), 2.64–2.84 (3H, m), 3.90 (2H, d, J=6.3 Hz), 4.08 (2H, q, J=6.9 Hz), 5.39–5.45 (1H, m), 6.19 (1H, d, J=1.6 Hz), 6.25–6.33 (1H, m), 6.41 (1H, dd, J=7.6, 1.6 Hz), 6.76–6.84 (2H, m), 7.51 (1H, dd, J=9.1, 3.2 Hz), 7.75–7.90 (1.5H, br), 7.97 (1H, d, J=3.2 Hz), 8.30–8.70 (1.5H, br)

Example 8

3-[2-[[2-[2-(5-Carbamimidoyl-2-hydroxybenzenesulfonylamino)ethyl]-5-isopropylphenyl]amino]acetylamino]propionic acid hydrochloride (Compound 15)

To a solution of 0.219 g of ethyl 3-[2-[[2-[2-(5-carbamimidoyl-2-hydroxybenzenesulfonylamino)ethyl]-5-isopropylphenyl]amino]acetylamino]propionate in 2.0 mL of tetrahydrofuran was added 2.05 mL of 1 mol/L sodium hydroxide solution, and the mixture was stirred at room temperature for 3 hours. To the reaction mixture was added 2.1 mL of 1 mol/L hydrochloric acid, and the solvent was removed under reduced pressure. The residue was purified by column chromatography on octadecyl silica gel (eluent: water-acetonitrile-1 mol/L hydrochloric acid) to give 0.107 g of 3-[2-[[2-[2-(5-crbamimidoyl-2-hydroxybenzenesulfonylamino)ethyl]-5-isopropylphenyl]amino]acetylamino] propionic acid hydrochloride.

$^1$H-NMR (DMSO-$d_6$) δ ppm: 1.12 (6H, d, J=6.9 Hz), 2.33–2.40 (2H, m), 2.60-2.70 (2H, m), 2.82–2.94 (1H, m), 2.95–3.17 (4H, m), 3.64–3.75 (2H, s), 6.36 (1H, s), 6.55 (1H, d, J=6.9 Hz), 6.88 (1H, d, J=6.9 Hz), 7.18–7.27 (1H, m), 7.72 (1H, d, J=8.2 Hz), 7.98 (1H, d, J=8.2 Hz), 8.19 (1H, s), 8.99–9.24 (2H, m), 9.29–9.50 (2H, m), 10.00–10.90 (1H, m), 11.85–12.65 (2H, m)

Example 9

The following compounds were prepared according to a similar manner to that described in Example 8

[[[2-[2-(5-Carbamimidoyl-2-hydroxybenzenesulfonylamino)ethyl]-5-isopropylphenyl]aminooxalyl]amino]acetic acid hydrochloride (Compound 16)

$^1$H-NMR (DMSO-$d_6$) δ ppm: 1.16 (6H, d, J=6.9 Hz), 2.59–2.69 (2H, m), 2.83 (1H, sept, J=6.9 Hz), 2.92–3.04 (2H, m), 3.89 (2H, d, J=6.3 Hz), 7.06 (1H, dd, J=7.9, 1.6 Hz), 7.11 (1H, d, J=7.9 Hz), 7.16 (1H, d, J=1.6 Hz), 7.19 (1H, d, J=8.8 Hz), 7.49 (1H, t, J=5.7 Hz), 7.87 (1H, dd, J=8.8, 2.5 Hz), 8.13 (1H, d, J=2.5 Hz), 8.90 (2H, br s), 9.03 (1H, t, J=6.3 Hz), 9.24 (2H, br s), 10.18 (1H, br s), 12.04 (1H, br s). 12.60–13.00 (1H, br)

[[4-[2-(5-Carbamimidoyl-2-hydroxybenzenesulfonylamino)ethyl]-2'-methanesulfonylbiphenyl-3-yl] amino]acetic aid hydrochloride (Compound 17)

$^1$H-NMR (DMSO-$d_6$) δ ppm: 2.65–2.80 (5H, m), 3.00–3.10 (2H, m), 3.82 (2H, s), 6.40–6.45 (1H, m), 6.55–6.60 (1H, m), 6.99 (1H, d, J=7.6 Hz), 7.24 (1H, d, J=8.8 Hz), 7.30–7.45 (2H, m), 7.60–7.75 (2H, m), 7.87–7.92 (1H, m), 8.04–8.07 (1H, m), 8.15–8.20 (1H, m), 8.89 (3H, br s), 9.29 (3H, br s), 12.15 (1H, br s)

[[2-[2-(5-Carbamimidoyl-2-hydroxybenzenesulfonylamino)ethyl]-5-isopropylphenyl]amino]acetic acid (Compound 18)

$^1$H-NMR (DMSO-$d_6$) δ ppm: 1.12 (6H, d, J=6.9 Hz), 2.55–2.61 (3H, m), 2.82-2.90 (2H, m), 3.70 (2H, s), 6.22 (1H, d, J=1.6 Hz), 6.39 (1H, dd, J=7.6, 1.6 Hz), 6.48 (1H, d, J=9.1 Hz), 6.79 (1H, d, J=7.6 Hz), 7.58 (1H, dd, J=9.1, 2.8 Hz), 7.91–8.01 (3H, m), 8.75–8.95 (2H, m)

Example 10

The following compounds were prepared according to the similar manner to that described in Example 6 and 8 without isolation of the intermediate 3-[[2-[2-(5-Carbamimidoyl-2-hydroxybenzenesulfonylamino)ethyl]-5-isopropylphenyl]carbamoyl]-2,3-dihyroxypropionic acid hydrochloride (Compound 19)

$^1$H-NMR (DMSO-$d_6$) δ ppm: 1.16 (6H, d, J=6.9 Hz), 2.60–2.70 (2H, m), 2.72-2.89 (1H, m), 2.92–3.02 (2H, m), 4.40–4.43 (2H, m), 6.87 (1H, br s), 6.98 (1H, dd, J=7.9, 1.9 Hz), 7.05 (1H, d, J=7.9 Hz), 7.18 (1H, d, J=8.8 Hz), 7.32 (1H, d, J=1.9 Hz), 7.34 (1H, t, J=5.7 Hz), 7.86 (1H, dd, J=8.8, 2.2 Hz), 8.13 (1H, d, J=2.2 Hz), 8.81 (2H, br s), 9.10 (1H, br s), 9.24 (2H, br s), 11.99 (1H, br s)

[[2-[2-(5-Carbamimidoyl-2-hydroxybenzenesulfonylamino)ethyl]-5-isopropylphenyl](ethyl)sulfamoyl]acetic acid hydrochloride (Compound 20)

$^1$H-NMR (CD$_3$CN) δ ppm: 1.20 (6H, d, J=6.9 Hz), 1.34 (3H, t, J=7.3 Hz), 2.78–3.00 (4H, m), 3.19–3.33 (5H, m), 6.91–7.00 (1H, m), 7.06–7.27 (3H, m), 7.71 (1H, dd, J=8.5, 2.2 Hz), 7.74–7.90 (1H, m), 8.00–8.17 (2H, br), 8.20–8.35 (1H, m), 8.62–8.86 (2H, m)

N-[2-[2-(5-Carbamimidoyl-2-hydroxybenzenesulfonylamino)ethyl]-5-isopropylphenyl]oxalamic acid (Compound 21)

$^1$H-NMR (DMSO-$d_6$) δ ppm: 1.15 (6H, d, J=6.9 Hz), 2.60–2.69 (2H, m), 2.75–2.97 (3H, m), 7.01–7.13 (3H, m), 7.25 (1H, d, J=8.5 Hz), 7.47 (1H, t, J=6.0 Hz), 7.89 (1H, dd, J=8.5, 2.2 Hz), 8.16 (1H, d, J=2.2 Hz), 9.04 (2H, br s), 9.27 (2H, br s), 10.27 (1H, br s), 12.13 (1H, br s)

Example 11

N-[2-[2-(5-Carbamimidoyl-2-hydroxybenzenesulfonylamino)ethyl]-5-isopropylphenyl]-2-(1-ethyl-1H-tetrazol-5-yl)acetamide (Compound 22)

A solution of 0.112 g of N-[2-[2-(5-cyano-2-methoxybenzenesulfonylamino)ethyl]-5-isopropylphenyl]-2-(1-ethyl-1H-tetrazol-5-yl)acetamide and 28 mg of lithium chloride in 0.65 mL of N,N-dimethylformamide was stirred at 140° C. for 4 hours. To the reaction mixture were added 1 mol/L hydrochloric acid and ethyl acetate, and the mixture was separated. The aqueous layer was extracted with ethyl acetate, and the organic layers were combined. After the organic layer was washed with water, and brine, dried over anhydrous magnesium sulfate, and the solvent was removed under reduced pressure. The residue was dissolved in 2.5 mL of 39% hydrogen chloride-ethanol solution, and the solution was stirred at room temperature for 5 hours. The reaction mixture was concentrated under reduced pressure, and the residue was dissolved in 1.0 mL of ethanol. To the solution was added 66 mg of ammonium acetate, and the mixture was stirred at room temperature for 14 hours. To the reaction mixture were added water, ethyl acetate, and hexane, and the precipitate was collected by filtration to give 42 mg of N-[2-[2-(5-carbamimidoyl-2-hydroxybenzenesulfonylamino)ethyl]-5-isopropylphenyl]-2-(1-ethyl-1H-tetrazol-5-yl)acetamide.

$^1$H-NMR (DMSO-$d_6$) δ ppm: 1.15 (6H, d, J=6.9 Hz), 1.46 (3H, t, J=7.3 Hz), 2.69–2.91 (5H, m), 4.34 (2H, s), 4.42 (2H, q, J=7.3 Hz), 6.34 (1H, d, J=9.1 Hz), 6.86–6.94 (1H, br), 7.00 (1H, dd, J=7.9, 1.6 Hz), 7.10 (1H, d, J=7.9 Hz), 7.28 (1H, d, J=1.6 Hz), 7.52 (1H, dd, J =9.1, 3.2 Hz), 7.60–8.10 (3H, m), 8.30–8.70 (2H, br), 10.00 (1H, br s)

Example 12

The following compound was prepared according to a similar manner to that described in Example 11, and isolated as hydrochloride salt by means of the usual manner N-[2-[2-(5-Carbamimidoyl-2-hydroxybenzenesulfonylamino)ethyl]-5-isopropylphenyl]-2-(1H-tetrazol-5-yl)acetamide hydrochloride (Compound 23)

$^1$H-NMR (DMSO-$d_6$) δ ppm: 1.12 (6H, d, J=6.9 Hz), 2.66–2.84 (5H, m), 4.12 (2H, s), 6.92–7.02 (2H, m), 7.06–7.14 (2H, m), 7.66 (1H, dd, J=8.9, 2.5 Hz), 8.03 (1H, d, J=2.5 Hz), 8.29 (2H, br s), 8.89 (2H, br s), 9.60 (1H, br s)

Example 13

Ethyl [[2-[2-[5-(N-hydroxycarbamimidoyl-2-hydroxybenzenesulfonylamino)ethyl]-5-isopropylphenyl]amino]acetate (Compound 24)

Ethyl [[2-[2-(5-cyano-2-hydroxybenzenesulfonylamino)ethyl]-5-isopropylphenyl]amino]acetate (0.19 g) was dissolved in 3.5 mL of 30% hydrogen chloride-ethanol solution, and the solution was stirred at room temperature for 5.8 hours. The solvent was removed under reduced pressure, and the residue was dissolved in 2.0 mL of ethanol. To the solution was added 0.238 g of hydroxylammonium acetate, and the mixture was stirred at room temperature for 38 hours. The solvent was removed under reduced pressure, and the residue was dissolved in water and ethyl acetate. The separated organic layer was washed with water and brine, and dried over anhydrous magnesium sulfate. The solvent was removed under reduced pressure, and the residue was purified by column chromatography on silica gel (eluent: ethyl acetate-hexane) to give 0.120 g of ethyl [[2-[2-[5-(N-hydroxycarbamimidoyl-2-hydroxybenzenesulfonylamino)ethyl]-5-isopropylphenyl]amino]acetate.

$^1$H-NMR (DMSO-$d_6$) δ ppm: 1.20 (6H, d, J=6.9 Hz), 1.31 (3H, t, J=7.3 Hz), 2.70 (2H, t, J=6.6 Hz), 2.80 (1H, sept, J=6.9 Hz), 3.26 (2H, t, J=6.6 Hz), 3.96 (2H, s), 4.26 (2H, q, J=7.3 Hz), 4.31–4.50 (1H, br), 4.87 (2H, br s), 5.50–5.70 (1H, br), 6.37 (1H, d, J=1.6 Hz), 6.60 (1H, dd, J=7.9, 1.6 Hz), 6.87 (1H, d, J=7.9 Hz), 7.00 (1H, d, J=8.8 Hz), 7.71 (1H, dd, J=8.8, 2.2 Hz), 7.93 (1H, d, J=2.2 Hz)

Test Example 1

Measurement of Inhibitory Activity for Activated Blood Coagulation Factor X 2.5 µL of a dimethylsulfoxide solution of a test compound, 187.5 µL of 100 mM tris-200 mM NaCl buffer (pH 8.4) and 50 µL of 1 mM S-2222 (Daiichi Pure Chemicals) aqueous solution were poured into 96 well microplate. Then 10 µL of 0.6 U/mL human activated blood coagulation factor X (Calbiochem) in gelatin-glycine buffer was added and the mixture was incubated for 10 minutes at 37° C. The reaction was terminated with the addition of 50 µL of 60% acetic acid and absorbance (405 nm) was measured by a microplate reader (SPECTRAmax250, Molecular Devices).

The group with 2.5 µL of the dimethylsulfoxide solution instead of the test compound solution was defined as the control, and the group with 10 µL of the gelatin-glycine buffer solution instead of human activated blood coagulation factor X was defined as the blank. The concentration of a test compound that inhibited the absorbance of control by 50% ($IC_{50}$) was obtained, and this value was used as the index of inhibitory activity for activated blood coagulation factor X. Results were shown as Table 1.

TABLE 1

| Test compound No. | Inhibitory activity for activated blood coagulation factor X ($IC_{50}$, µM) |
| --- | --- |
| Compound 17 | 0.0071 |
| Compound 18 | 0.077 |

Test Example 2

Measurement of Inhibitory Activity for Thrombin 2.5 µL of a dimethylsulfoxide solution of a test compound, 187.5 µL of 100 mM tris-200 mM NaCl buffer (pH 8.4) and 50 µL of 1 mM S-2238 (Daiichi Pure Chemicals) aqueous solution were poured into 96 well microplate. Then 10 µL of 2.0 U/mL human thrombin (Sigma Chemical Company) in gelatin-glycine buffer was added and the mixture was incubated for 10 minutes at 37° C. The reaction was terminated with the addition of 50 µL of 60% acetic acid and absorbance (405 nm) was measured by a microplate reader (SPECTRAmax250, Molecular Devices).

The group with 2.5 µL of the dimethylsulfoxide solution instead of the test compound solution was defined as the control, and the group with 10 µL of the gelatin-glycine buffer solution instead of human thrombin was defined as the blank. The concentration of a test compound that inhibited the absorbance of control by 50% ($IC_{50}$) was obtained, and this value was used as the index of inhibitory activity for thrombin. Results were shown as Table 2.

TABLE 2

| Test compound No. | Inhibitory activity for thrombin ($IC_{50}$, µM) |
| --- | --- |
| Compound 17 | 37 |
| Compound 18 | >100 |

INDUSTRIAL APPLICABILITY

The 5-amidino-N-(2-aminophenethyl)-2-hydroxybenzenesulfonamide derivatives and pharmaceutically acceptable salts thereof of present inventors show a potent and selective activated blood coagulation factor X inhibitory activity. The present invention can provide novel compounds having excellent properties as activated blood coagulation factor X inhibitors. In addition, the 5-cyano-N-(2-aminophenethyl)-2-hydroxybenzenesulfonamide derivatives represented by the above general formulae (II) and salts thereof of the present invention are important as intermediates in the production of the compounds represented by the above general formula (I). Accordingly, the compounds represented by the above general formula (I) of the present invention can be readily prepared via these compounds.

The invention claimed is:
1. A 5-amidino-N-(2-aminophenethyl)-2-hydroxybenzenesulfonamide derivative represented by the general formula:

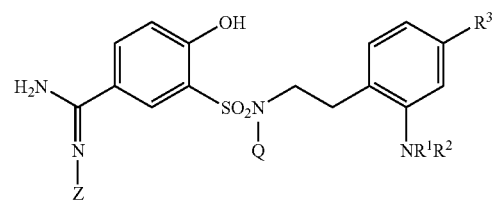

wherein $R^1$ represents a hydrogen atom or a lower alkyl group;
$R^2$ represents a hydrogen atom, a lower alkyl group, —$Y^1$—COO$R^A$ in which $Y^1$ represents a lower alkylene group or a single bond; and $R^A$ represents a hydrogen atom or a lower alkyl group, —COCOO$R^B$ in which $R^B$ represents a hydrogen atom or a lower alkyl group, —$Y^2$—CONH—$R^C$ in which $Y^2$ represents a lower alkylene group or a single bond; and $R^C$ represents a hydrogen atom, or a lower alkyl group which may have a substituent selected from the following group (i), —COCONH—$R^D$ in which $R^D$ is a hydrogen atom or a lower alkyl group which may have a substituent selected from the following group (ii), —CO—$Y^3$—$R^E$ in which $Y^3$ is a lower alkylene group or a single bond; and $R^E$ represents a 5 to 10-membered aromatic heterocyclic group which may have a lower alkyl group, —CO—$Y^4$—$R^F$ in which $Y^4$ is a lower alkylene group which may have one or two hydroxy groups; and $R^F$ represents a —COO$R^{F1}$ in which $R^{F1}$ is a hydrogen atom or a lower alkyl group, or a lower alkylsulfonyl group which may have —COO$R^G$ where $R^G$ is a hydrogen atom or a lower alkyl group;
(i) —COO$R^{C1}$ in which $R^{C1}$ is a hydrogen atom or a lower alkyl group;
(ii) —COO$R^{D1}$ in which $R^{D1}$ is a hydrogen atom or a lower alkyl group;
$R^3$ represents a di(lower alkyl)amino group, a lower alkyl group, a 3 to 10-membered cycloalkyl group, a 6 to 10-membered aryl group which may have one to three substituents selected from the following group (A), a 3 to 10-membered heterocycloalkyl group which may have an oxo group, or a 5 to 10-membered aromatic heterocyclic group which may have a substituent selected from the following group (B);
(A) an oxo group, a lower alkyl group, a halo(lower alkyl)group, —$Y^5$—$R^H$, a halogen atom, a nitro group, an amino group, —COO$R^I$, a carbamoyl group, a sulfamoyl group, a lower alkylsulfonyl group, a mono (lower alkyl)sulfamoyl group which may have —COO$R^J$, and a lower alkylsulfonylamino-substituted (lower alkyl) group;
wherein $Y^5$ represents an oxygen atom or a sulfur atom;
$R^H$ represents a hydrogen atom, a halo(lower alkyl) group or a lower alkyl group which may have —COO$R^{H1}$ in which $R^{H1}$ is a hydrogen atom, a 3 to 10-membered heterocycloalkyl group or a lower alkyl group;
$R^I$ represents a hydrogen atom, a 3 to 10-membered cycloalkyl group or a lower alkyl group;
$R^J$ represents a hydrogen atom, a 3 to 10-membered cycloalkyl group or a lower alkyl group;

(B) a lower alkyl group, an amino group and —COOR$^K$;
wherein R$^K$ represents a hydrogen atom, a 3 to 10-membered cycloalkyl group and lower alkyl group;
Q represents a hydrogen atom or a lower alkyl group which may have a substituent selected from the following group (C);
(C) —OR$^L$, —COOR$^M$, —CONR$^N$R$^O$, a 6 to 10-membered aryl group which may have one to three substituents selected from the following group (iii), and a 5 to 10-membered aromatic heterocyclic group which may have one to three substituents selected from the following group (iv);
wherein R$^L$ represents a hydrogen atom or a lower alkyl group which may have —OR$^{L1}$ where R$^{L1}$ represents a hydrogen atom or a lower alkyl group; R$^M$ represents a hydrogen atom, a 3 to 10-membered cycloalkyl group, or a lower alkyl group which may have a substituent selected from the following group (v); R$^N$ and R$^O$ independently represent a hydrogen atom, a 6 to 10-membered aryl group which may have a carbamoyl group, a 5 to 10-membered aromatic heterocyclic group which may have a substituent selected from the following group (vi), or a lower alkyl group which may have a substituent selected from the following group (vii), or —NR$^N$R$^O$ forms a cyclic amino group which may have a substituent selected from the following group (viii);
(v) —COOR$^{M1}$ in which R$^{M1}$ is a hydrogen atom, a 3 to 10-membered cycloalkyl group or a lower alkyl group, —OCOR$^{M2}$ in which R$^{M2}$ is a 3 to 10-membered cycloalkyl group or a lower alkyl group, —OCOOR$^{M3}$ in which R$^{M3}$ is a 3 to 10-membered cycloalkyl group or a lower alkyl group, —OR$^{M4}$ in which R$^{M4}$ is a hydrogen atom, a 3 to 10-membered cycloalkyl group or a lower alkyl group, —CONR$^{M5}$R$^{M6}$ in which R$^{M5}$ and R$^{M6}$ are independently a hydrogen atom or a lower alkyl group, or —NR$^{M5}$R$^{M6}$ forms a cyclic amino group, a 3 to 10-membered cycloalkyl group, a 6 to 10-membered aryl group, a 3 to 10 membered heterocycloalkyl group, and a 5 to 10-membered aromatic heterocyclic group;
(vi) a halogen atom, a lower alkyl group, a carbamoyl group and —COOR$^{N1}$ in which R$^{N1}$ represents a hydrogen atom, or a lower alkyl group;
(vii) —OR$^{N2}$ in which R$^{N2}$ is a hydrogen atom or a lower alkyl group, and a 5 to 10-membered aromatic heterocyclic group;
(viii) a hydroxy group, a lower alkyl group, a hydroxy(lower alkyl) group, a carbamoyl group, a di(lower alkyl)amino group, a lower acyl group, and —COOR$^{N3}$ in which R$^{N3}$ represents a hydrogen atom or a lower alkyl group;
(iii) a halogen atom, a nitro group, a lower alkyl group, —OR$^P$ in which R$^P$ is a hydrogen atom or a lower alkyl group, and —COOR$^Q$ in which R$^Q$ is a hydrogen atom or a lower alkyl group;
(iv) a halogen atom, an oxo group, a lower alkyl group and a phenyl group; and Z represents a hydrogen atom, a hydroxy group or —COOR$^R$;
wherein R$^R$ is a halo(lower alkyl) group, a 6 to 10-membered aryl group or a lower alkyl group which may have a substituent selected from the following group (ix);
(ix) —OR$^{R1}$ in which R$^{R1}$ is a hydrogen atom or a lower alkyl group, —COOR$^{R2}$ in which R$^{R2}$ is a lower alkyl group which may have —COOR$^{R21}$ where R$^{R21}$ is a lower alkyl group, —CONR$^{R3}$R$^{R4}$ in which R$^{R3}$ and R$^{R4}$ are independently a hydrogen atom or a lower alkyl group, or —NR$^{R3}$R$^{R4}$ forms a cyclic amino group, —OCOR$^{R5}$ in which R$^{R5}$ is a lower alkyl group which may have —OCOR$^{R51}$ where R$^{R51}$ is a lower alkyl group, a 3 to 10-membered heterocycloalkyl group and a 6 to 10-membered aryl group;
or a pharmaceutically acceptable salt thereof.

2. A 5-amidino-N-(2-aminophenethyl)-2-hydroxybenzenesulfonamide derivative as claimed in claim 1, represented by the general formula:

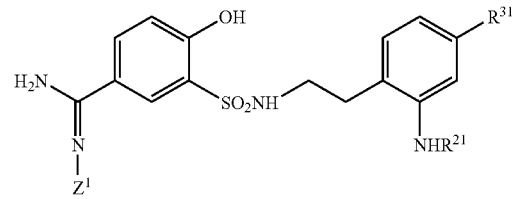

wherein R$^{21}$ represents —Y$^{11}$—COOR$^4$ in which Y$^{11}$ is a lower alkylene group; and R$^4$ is a hydrogen atom or a lower alkyl group;
R$^{31}$ represents a 6 to 10-membered aryl group which may have one to three substituents selected from the following group (A);
(A) an oxo group, a lower alkyl group, a halo(lower alkyl)group, —Y$^5$—R$^H$, a halogen atom, a nitro group, an amino group, —COOR$^J$, a carbamoyl group, a sulfamoyl group, a loweralkylsulfonyl group, a mono(lower alkyl)sulfamoyl group which may have —COOR$^J$, and a loweralkylsulfonylamino-substituted (lower alkyl) group;
wherein Y$^5$ represents an oxygen atom or a sulfur atom;
R$^H$ represents a hydrogen atom, a halo(lower alkyl) group, or a lower alkyl group which may have —COOR$^{H1}$ where R$^{H1}$ is a hydrogen atom, a 3 to 10-membered heterocycloalkyl or a lower alkyl group;
R$^1$ represents a hydrogen atom, a 3 to 10-membered cycloalkyl group or a lower alkyl group;
R$^J$ represents a hydrogen atom, a 3 to 10-membered cycloalkyl group, or lower alkyl group;
Z$^1$ represents a hydroxy group or —COOR$^R$; wherein R$^R$ is a halo(lower alkyl) group, a 6 to 10-membered aryl group or a lower alkyl group which may have a substituent selected from the following group (ix);
(ix) —OR$^{R1}$ in which R$^{R1}$ is a hydrogen atom or a lower alkyl group, —COOR$^{R2}$ in which R$^{R2}$ is a lower alkyl group which may have —COOR$^{R21}$ where R$^{R21}$ is a lower alkyl group, —CONR$^{R3}$R$^{R4}$ in which R$^{R3}$ and R$^{R4}$ are independently a hydrogen atom or a lower alkyl group, or —NR$^{R3}$R$^{R4}$ forms a cyclic amino group, —OCOR$^{R5}$ in which R$^{R5}$ is a lower alkyl group which may have —OCOR$^{R51}$ where R$^{R51}$ is a lower alkyl group, a 3 to 10-membered heterocycloalkyl group and a 6 to 10-membered aryl group;
or a pharmaceutically acceptable salt thereof.

3. A pharmaceutical composition comprising as an active ingredient a 5-amidino-N-(2-aminophenethyl)-2-hydroxybenzenesulfonamide derivative as claimed in claim 1, or a pharmaceutically acceptable salt thereof.

4. An activated blood coagulation factor X inhibitor consisting of as an active ingredient a 5-amidino-N-(2-aminophenethyl)-2-hydroxybenzenesulfonamide derivative as claimed in claim 1, or a pharmaceutically acceptable salt thereof.

5. A composition for the treatment of a disease requiring the inhibition of an activated blood coagulation factor X consisting of as an active ingredient a 5-amidino-N-(2-aminophenethyl)-2-hydroxybenzenesulfonamide derivative as claimed in claim 1, or a pharmaceutically acceptable salt thereof.

6. A composition for the treatment as claimed in claim 5 wherein the disease requiring inhibition of an activated blood coagulation factor X is a disease selected from the group consisting of cerebral infarction, cerebral thrombosis, cerebral embolism, transient cerebral ischemic attack, subarachnoid hemorrhage-induced cerebral vasospasm, alzheimer's disease, myocardial infarction, unstable angina, heart failure, thrombosis followed by atrial fibrillation, pulmonary infarction, pulmonary embolism, acute respiratory distress syndrome, Berger disease, peripheral arterial obstruction, deep vein thrombosis, disseminated intravascular coagulation syndrome, atherosclerosis, behcet's disease, diabetic neuropathy, diabetic nephropathy, diabetic retinopathy, diabetic thrombotic complications, acute progressive glomerulonephritis, chronic glomerulonephritis, IgA nephropathy, nephritic syndrome, focal segmental glomerulosclreosis, membranous nephropathy, membranoproliferative glomerulonephritis, crescentic glomerulonephritis, lupus nephritis, purpura nephritis, interplanting rejection, systemic inflammatory response syndrome, dialysis- or operation-induced thrombocytopenia, thrombus formation after artificial blood vessel operation or after artificial valve replacement, restenosis and reocculusion after coronary intervention, thrombus formation at the time of extracorporeal circulation, blood coagulation at the time of insertion of blood vessel catheter and influenza virus infection.

7. A method for the treatment of a disease requiring inhibition of an activated blood coagulation factor X, which comprises administering a therapeutically effective amount of a 5-amidino-N-(2-aminophenethyl)-2-hydroxybenzenesulfonamide derivative as claimed in claim 1, or a pharmaceutically acceptable salt thereof.

8. A method for the manufacture of a pharmaceutical composition for the treatment of a disease requiring the inhibition of an activated blood factor X which comprises mixing a 5-amidino-N-(2-aminophenethyl)-2-hydroxybenzenesulfonamide derivative as claimed in claim 1, or a pharmaceutically acceptable salt thereof with pharmaceutical additives.

9. A pharmaceutical composition which comprises (a) a 5-amidino-N-(2-aminophenethyl)-2-hydroxybenzenesulfonamide derivative as claimed in claim 1, or a pharmaceutically acceptable salt thereof, and (b) at least one member selected from the group consisting of adrenocortical hormone, platelet aggregation inhibitors, adenylate cyclase activators, PGF2α antagonists, cyclooxygenase inhibitors, adenosine antagonists, GPIIb/IIIa antagonists, anticoagulants, thrombolitic drugs, antithrombin drugs, free-radical scavengers, immunosuppressant drugs, erythropoietin, fish oil, angiotensin-converting enzyme inhibitors, angiotensin II receptor antagonists, glycation inhibitors, protein kinase C inhibitors, aldose reductase inhibitors, endothelin receptor antagonists, endothelin-converting enzyme inhibitors, neutral endopeptidase inhibitors, thromboxane $A_2$ synthetase inhibitors, thromboxane $A_2$ receptor antagonists and $PGI_2$ agonists.

10. An activated blood coagulation factor X inhibitor which comprises (a) a 5-amidino-N-(2-aminophenethyl)-2-hydroxybenzenesulfonamide derivative as claimed in claim 1, or a pharmaceutically acceptable salt thereof, and (b) at least one member selected from the group consisting of adrenocortical hormone, platelet aggregation inhibitors, adenylate cyclase activators, PGF2α antagonists, cyclooxygenase inhibitors, adenosine antagonists, GPIIb/IIIa antagonists, anticoagulants, thrombolitic drugs, antithrombin drugs, free-radical scavengers, immunosuppressant drugs, erythropoietin, fish oil, angiotensin-converting enzyme inhibitors, angiotensin II receptor antagonists, glycation inhibitors, protein kinase C inhibitors, aldose reductase inhibitors, endothelin receptor antagonists, endothelin-converting enzyme inhibitors, neutral endopeptidase inhibitors, thromboxane $A_2$ synthetase inhibitors, thromboxane $A_2$ receptor antagonists and $PGI_2$ agonists.

11. A composition for the treatment of a disease requiring inhibition of an activated blood coagulation factor X which comprises (a) a 5-amidino-N-(2-aminophenethyl)-2-hydroxybenzenesulfonamide derivative as claimed in claim 1, or a pharmaceutically acceptable salt thereof, and (b) at least one member selected from the group consisting of adrenocortical hormone, platelet aggregation inhibitors, adenylate cyclase activators, PGF2α antagonists, cyclooxygenase inhibitors, adenosine antagonists, GPIIb/IIIa antagonists, anticoagulants, thrombolitic drugs, antithrombin drugs, free radical scavengers, immunosuppressant drugs, erythropoietin, fish oil, angiotensin-converting enzyme inhibitors, angiotensin II receptor antagonists, glycation inhibitors, protein kinase C inhibitors, aldose reductase inhibitors, endothelin receptor antagonists, endothelin-converting enzyme inhibitors, neutral endopeptidase inhibitors, thromboxane $A_2$ synthetase inhibitors, thromboxane $A_2$ receptor antagonists and $PGI_2$ agonists.

12. A method for the treatment of a disease requiring inhibition of an activated blood coagulation factor X, which comprises administering an effective amount of (a) a 5-amidino-N-(2-aminophenethyl)-2-hydroxybenzenesulfonamide derivative as claimed in claim 1, or a pharmaceutically acceptable salt thereof, in combination with (b) one drug at least selected from the group consisting of adrenocortical hormone, platelet aggregation inhibitors, adenylate cyclase activators, PGF2α antagonists, cyclooxygenase inhibitors, adenosine antagonists, GPIIb/IIIa antagonists, anticoagulants, thrombolitic drugs, antithrombin drugs, free-radical scavengers, immunosuppressant drugs, erythropoietin, fish oil, angiotensin-converting enzyme inhibitors, angiotensin II receptor antagonists, glycation inhibitors, protein kinase C inhibitors, aldose reductase inhibitors, endothelin receptor antagonists, endothelin-converting enzyme inhibitors, neutral endopeptidase inhibitors, thromboxane $A_2$ synthetase inhibitors, thromboxane $A_2$ receptor antagonists and $PGI_2$ agonists.

13. A method for the manufacture of a pharmaceutical composition for the treatment of a disease requiring the inhibition of an activated blood factor X which comprises mixing (a) a 5-amidino-N-(2-aminophenethyl)-2-hydroxybenzenesulfonamide derivative as claimed in claim 1, or a pharmaceutically acceptable salt thereof, and (b) one drug at least selected from the group consisting of adrenocortical hormone, platelet aggregation inhibitors, adenylate cyclase activators, PGF2α antagonists, cyclooxygenase inhibitors, adenosine antagonists, GPIIb/IIIa antagonists, anticoagulants, thrombolitic drugs, antithrombin drugs, free-radical scavengers, immunosuppressant drugs, erythropoietin, fish oil, angiotensin-converting enzyme inhibitors, angiotensin II receptor antagonists, glycation inhibitors, protein kinase C inhibitors, aldose reductase inhibitors, endothelin receptor antagonists, endothelin-converting enzyme inhibitors, neutral endopeptidase inhibitors, thromboxane $A_2$ synthetase inhibitors, thromboxane $A_2$ receptor antagonists and $PGI_2$ agonists, with pharmaceutical additives.

14. A pharmaceutical composition comprising as an active ingredient a 5-amidino-N-(2-aminophenethyl)-2-hydroxybenzenesulfonamide derivative as claimed in claim 2, or a pharmaceutically acceptable salt thereof.

15. An activated blood coagulation factor X inhibitor consisting of as an active ingredient a 5-amidino-N-(2-aminophenethyl)-2-hydroxybenzenesulfonamide derivative as claimed in claim 2, or a pharmaceutically acceptable salt thereof.

16. A composition for the treatment of a disease requiring inhibition of an activated blood coagulation factor X consisting of as an active ingredient a 5-amidino-N-(2-aminophenethyl)-2-hydroxybenzenesulfonamide derivative as claimed in claim 2, or a pharmaceutically acceptable salt thereof.

17. A composition for the treatment as claimed in claim 16 wherein the disease requiring inhibition of an activated blood coagulation factor X is a disease selected from the group consisting of cerebral infarction, cerebral thrombosis, cerebral embolism, transient cerebral ischemic attack, subarachnoid hemorrhage-induced cerebral vasospasm, alzheimer's disease, myocardial infarction, unstable angina, heart failure, thrombosis followed by atrial fibrillation, pulmonary infarction, pulmonary embolism, acute respiratory distress syndrome, Berger disease, peripheral arterial obstruction, deep vein thrombosis, disseminated intravascular coagulation syndrome, atherosclerosis, behcet's disease, diabetic neuropathy, diabetic nephropathy, diabetic retinopathy, diabetic thrombotic complications, acute progressive glomerulonephritis, chronic glomerulonephritis, IgA nephropathy, nephritic syndrome, focal segmental glomerulosclreosis, membranous nephropathy, membranoproliferative glomerulonephritis, crescentic glomerulonephritis, lupus nephritis, purpura nephritis, interplanting rejection, systemic inflammatory response syndrome, dialysis- or operation-induced thrombocytopenia, thrombus formation after artificial blood vessel operation or after artificial valve replacement, restenosis and reocculusion after coronary intervention, thrombus formation at the time of extracorporeal circulation, blood coagulation at the time of insertion of blood vessel catheter and influenza virus infection.

18. A method for the treatment of a disease requiring inhibition of an activated blood coagulation factor X, which comprises administering a therapeutically effective amount of a 5-amidino-N-(2-aminophenethyl)-2-hydroxybenzenesulfonamide derivative as claimed in claim 2, or a pharmaceutically acceptable salt thereof.

19. A method for the manufacture of a pharmaceutical composition for the treatment of a disease requiring the inhibition of an activated blood factor X which comprises mixing a 5-amidino-N-(2-aminophenethyl)-2-hydroxybenzenesulfonamide derivative as claimed in claim 2, or a pharmaceutically acceptable salt thereof with pharmaceutical additives.

20. A pharmaceutical composition which comprises (a) a 5-amidino-N-(2-aminophenethyl)-2-hydroxybenzenesulfonamide derivative as claimed in claim 2, or a pharmaceutically acceptable salt thereof, and (b) at least one member selected from the group consisting of adrenocortical hormone, platelet aggregation inhibitors, adenylate cyclase activators, PGF2α antagonists, cyclooxygenase inhibitors, adenosine antagonists, GPIIb/IIIa antagonists, anticoagulants, thrombolitic drugs, antithrombin drugs, free-radical scavengers, immunosuppressant drugs, erythropoietin, fish oil, angiotensin-converting enzyme inhibitors, angiotensin II receptor antagonists, glycation inhibitors, protein kinase C inhibitors, aldose reductase inhibitors, endothelin receptor antagonists, endothelin-converting enzyme inhibitors, neutral endopeptidase inhibitors, thromboxane $A_2$ synthetase inhibitors, thromboxane $A_2$ receptor antagonists and $PGI_2$ agonists.

21. An activated blood coagulation factor X inhibitor which comprises (a) a 5-amidino-N-(2-aminophenethyl)-2-hydroxybenzenesulfonamide derivative as claimed in claim 2, or a pharmaceutically acceptable salt thereof, and (b) at least one member selected from the group consisting of adrenocortical hormone, platelet aggregation inhibitors, adenylate cyclase activators, PGF2α antagonists, cyclooxygenase inhibitors, adenosine antagonists, GPIIb/IIIa antagonists, anticoagulants, thrombolitic drugs, antithrombin drugs, free-radical scavengers, immunosuppressant drugs, erythropoietin, fish oil, angiotensin-converting enzyme inhibitors, angiotensin II receptor antagonists, glycation inhibitors, protein kinase C inhibitors, aldose reductase inhibitors, endothelin receptor antagonists, endothelin-converting enzyme inhibitors, neutral endopeptidase inhibitors, thromboxane $A_2$ synthetase inhibitors, thromboxane $A_2$ receptor antagonists and $PGI_2$ agonists.

22. A composition for the treatment of a disease requiring inhibition of an activated blood coagulation factor X which comprises (a) a 5-amidino-N-(2-aminophenethyl)-2-hydroxybenzenesulfonamide derivative as claimed in claim 2, or a pharmaceutically acceptable salt thereof, and (b) at least one member selected from the group consisting of adrenocortical hormone, platelet aggregation inhibitors, adenylate cyclase activators, PGF2α antagonists, cyclooxygenase inhibitors, adenosine antagonists, GPIIb/IIIa antagonists, anticoagulants, thrombolitic drugs, antithrombin drugs, free radical scavengers, immunosuppressant drugs, erythropoietin, fish oil, angiotensin-converting enzyme inhibitors, angiotensin II receptor antagonists, glycation inhibitors, protein kinase C inhibitors, aldose reductase inhibitors, endothelin receptor antagonists, endothelin-converting enzyme inhibitors, neutral endopeptidase inhibitors, thromboxane $A_2$ synthetase inhibitors, thromboxane $A_2$ receptor antagonists and $PGI_2$ agonists.

23. A method for the treatment of a disease requiring inhibition of an activated blood coagulation actor X, which comprises administering an effective amount of (a) a 5-amidino-N-(2-aminophenethyl)-2-hydroxybenzenesulfonamide derivative as claimed in claim 2, or a pharmaceutically acceptable salt thereof, in combination with (b) one drug at least selected from the group consisting of adrenocortical hormone, platelet aggregation inhibitors, adenylate cyclase activators, PGF2α antagonists, cyclooxygenase inhibitors, adenosine antagonists, GPIIb/IIIa antagonists, anticoagulants, thrombolitic drugs, antithrombin drugs, free-radical scavengers, immunosuppressant drugs, erythropoietin, fish oil, angiotensin-converting enzyme inhibitors, angiotensin II receptor antagonists, glycation inhibitors, protein kinase C inhibitors, aldose reductase inhibitors, endothelin receptor antagonists, endothelin-converting enzyme inhibitors, neutral endopeptidase inhibitors, thromboxane $A_2$ synthetase inhibitors, thromboxane $A_2$ receptor antagonists and $PGI_2$ agonists.

24. A method for the manufacture of a pharmaceutical composition for the treatment of a disease requiring the inhibition of an activated blood factor X which comprises mixing (a) a 5-amidino-N-(2-aminophenethyl)-2-hydroxybenzenesulfonamide derivative as claimed in claim 2, or a pharmaceutically acceptable salt thereof, and (b) one drug at least selected from the group consisting of adrenocortical hormone, platelet aggregation inhibitors, adenylate cyclase activators, PGF2α antagonists, cyclooxygenase inhibitors, adenosine antagonists, GPIIb/IIIa antagonists, anticoagulants, thrombolitic drugs, antithrombin drugs, free-radical scavengers, immunosuppressant drugs, erythropoietin, fish oil, angiotensin-converting enzyme inhibitors, angiotensin II receptor antagonists, glycation inhibitors, protein kinase C inhibitors, aldose reductase inhibitors, endothelin receptor antagonists, endothelin-converting enzyme inhibitors, neutral endopeptidase inhibitors, thromboxane $A_2$ synthetase inhibitors, thromboxane $A_2$ receptor antagonists and $PGI_2$ agonists, with pharmaceutical additives.

* * * * *